United States Patent
Suzuki et al.

(10) Patent No.: US 12,201,793 B2
(45) Date of Patent: Jan. 21, 2025

(54) GUIDE WIRE HOLDER

(71) Applicant: OLYMPUS CORPORATION, Hachioji (JP)

(72) Inventors: Takahiro Suzuki, Tokyo (JP); Tomofumi Katayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1056 days.

(21) Appl. No.: 17/112,003

(22) Filed: Dec. 4, 2020

(65) Prior Publication Data

US 2021/0085930 A1    Mar. 25, 2021

Related U.S. Application Data

(63) Continuation of application No. PCT/JP2018/027283, filed on Jul. 20, 2018.

(51) Int. Cl.
*A61M 25/09* (2006.01)
*A61F 2/966* (2013.01)
(Continued)

(52) U.S. Cl.
CPC ....... *A61M 25/09041* (2013.01); *A61F 2/966* (2013.01); *A61B 1/273* (2013.01);
(Continued)

(58) Field of Classification Search
CPC ............ A61M 25/09041; A61M 5/007; A61M 2025/015; A61F 2/966; A61F 2002/041; A61B 1/273
(Continued)

(56) References Cited

U.S. PATENT DOCUMENTS

2004/0039250 A1    2/2004   Tholfsen et al.
2004/0044350 A1    3/2004   Martin et al.
(Continued)

FOREIGN PATENT DOCUMENTS

EP    3 238 641 A1    11/2017
EP    3 238 642 A1    11/2017
(Continued)

OTHER PUBLICATIONS

Aug. 17, 2021 Office Action issued in Japanese Patent Application No. 2020-530882.
(Continued)

*Primary Examiner* — Phillip A Gray
(74) *Attorney, Agent, or Firm* — Oliff PLC

(57) ABSTRACT

A guide wire holder includes a sheath having a lumen, an operation wire inserted into the lumen and configured to be able to advance and retract in the lumen, and a hook continuous with a distal end of the operation wire, being formed to be bent in a convex shape toward a distal side, and protrudes from a distal end of the sheath. The sheath has a side surface extending from the distal end of the sheath to a proximal end side in a direction of the longitudinal axis. The hook intersects a ridge line of the side surface and forms a closed region closed by the hook and the ridge line in a front view. The guide wire holder is configured to hold the guide wire located outside the sheath in the closed region in a state that the hook is disposed at a retracted position at which the hook is retracted.

20 Claims, 18 Drawing Sheets

(51) Int. Cl.
    *A61B 1/273*     (2006.01)
    *A61F 2/04*     (2013.01)
    *A61M 5/00*     (2006.01)
    *A61M 25/01*     (2006.01)

(52) U.S. Cl.
    CPC ........ *A61F 2002/041* (2013.01); *A61M 5/007* (2013.01); *A61M 2025/015* (2013.01); *A61M 2025/09116* (2013.01); *A61M 2025/09125* (2013.01); *A61M 2025/09183* (2013.01); *A61M 2210/1057* (2013.01)

(58) Field of Classification Search
    USPC ........................................................ 604/528
    See application file for complete search history.

(56) References Cited

U.S. PATENT DOCUMENTS

| | | |
|---|---|---|
| 2013/0172855 A1 | 7/2013 | Wood et al. |
| 2016/0121083 A1 | 5/2016 | Yokota et al. |
| 2017/0232237 A1* | 8/2017 | Yokota ............. A61B 17/22031 604/264 |
| 2018/0042462 A1 | 2/2018 | Yanuma |

FOREIGN PATENT DOCUMENTS

| | | |
|---|---|---|
| JP | 2004-202006 A | 7/2004 |
| JP | 2015-506722 A | 3/2015 |
| JP | 2016-140630 A | 8/2016 |
| JP | 2017-169783 A | 9/2017 |
| WO | 2005/011788 A1 | 2/2005 |
| WO | 2013/071938 A1 | 5/2013 |
| WO | 2016/103897 A1 | 6/2016 |
| WO | 2016/103900 A1 | 6/2016 |

OTHER PUBLICATIONS

Oct. 23, 2018 International Search Report issued in International Application No. PCT/JP2018/027283.
Apr. 9, 2019 Search Report issused in International Patent Application No. PCT/JP2019/001430.
Mar. 25, 2022 Search Report issued in European Patent Application No. 19838277.2.
Dec. 8, 2023 Office Action issued in U.S. Appl. No. 17/150,655.

* cited by examiner

GUIDE WIRE HOLDER

Exemplary embodiments relate to a guide wire holder and a method for inserting the guide wire holder. This application is a continuation application based on International Patent Application No. PCT/JP 2018/027283 filed on Jul. 20, 2018, and the content of the PCT international application is incorporated herein by reference.

BACKGROUND

A method of introducing a medical device into a hollow organ using a guide wire during a treatment or an examination of the hollow organ of a human body is known (for example, US Patent Application Publication No. 2016/0121083). In this method, the guide wire may not be able to be inserted into the hollow organ when an opening of the hollow organ has an obstacle such as a stenosis or occlusion. For example, when the duodenal papilla is occluded, it is difficult to insert a guide wire into a target hollow organ such as the bile duct or the pancreatic duct via the duodenal papilla.

A method called a rendezvous method is known as a coping method in such a case. In the rendezvous method, the bile duct or pancreas is checked by observing an ultrasound image, and a puncture needle is punctured into an intrahepatic bile duct or an extrahepatic bile duct from the esophagus, stomach, and duodenum. A guide wire is inserted inside the puncture needle punctured into the bile duct, and a distal end of the guide wire is inserted inside the bile duct or the pancreatic duct. Then, the guide wire is pushed forward to pass through the duodenal papilla, and the distal end portion of the guide wire is caused to protrude into the duodenum. Then, while the distal end portion of the guide wire protruding from the papilla of the duodenum is checked with an endoscopic image, a part of the distal end portion of the guide wire is gripped by a grip portion of a treatment tool (for example, gripping forceps). The treatment tool is drawn into the papilla by pulling the guide wire in this state. Accordingly, for example, an indwelling object such as a stent is capable of being indwelled in the bile duct by using the treatment tool in which the stent covers the treatment tool and the treatment tool functions as a guide sheath.

In the rendezvous method, a treatment tool which captures the guide wire and is inserted into the duodenal papilla side along the guide wire has been studied in order to insert the treatment tool into the bile duct while damage to the papilla tissue is curbed. For example, an endoscopic catheter which has a cutout portion at a distal end portion of a sheath and holds a guide wire in the cutout portion is known (refer to Japanese Unexamined Patent Application, First Publication No. 2017-169783). The endoscope catheter has a constitution in which the guide wire is inserted into the cutout portion by pressing an opening of the cutout portion from the side diagonally outward therefrom against the guide wire, and the sheath is slid along the guide wire in this state.

SUMMARY

A guide wire holder can include a sheath having a lumen of which a central axis extends along a longitudinal axis, an operation wire which is inserted into the lumen and is constituted to be able to advance and retract in the lumen along the longitudinal axis, and a hook which is continuous with a distal end of the operation wire, is formed to be bent in a convex shape toward a distal side, and protrudes from a distal end of the sheath, wherein the sheath has a side surface which extends from the distal end of the sheath to a proximal side in a direction of the longitudinal axis, the hook intersects a ridge line of the side surface and forms a closed region closed by the hook and the ridge line in a front view seen in a direction along the longitudinal axis, and the guide wire located outside the sheath is able to be held in the closed region in a state in which the hook is disposed at a retracted position at which the hook is retracted.

In a guide wire holder, a pre-curved portion to which a bending tendency for bending in the direction of the longitudinal axis in a natural state is imparted may be provided at a distal end portion of the sheath, and the side surface may be located outside a curved shape of the pre-curved portion which has the bending tendency.

In a guide wire holder, the hook may include a first end portion which is formed by bending a wire-shaped member and connected to the distal end of the operation wire, and a second end portion which extends along the longitudinal axis toward a proximal side of the sheath, the hook may advance and retract on a distal end side of the sheath as the operation wire advances and retracts, the second end portion may be separated from the distal end of the sheath at an advanced position in which the hook is advanced, and the second end portion may be disposed close to the distal end of the sheath at the retracted position.

In a guide wire holder, the hook may be bent at a right angle or an obtuse angle with respect to the central axis of the lumen on a side surface side in a side view, and the hook may be configured to be able to capture the guide wire in a state in which the guide wire to be captured is arranged from the side surface toward the proximal end side of the sheath along the direction of the longitudinal axis.

In a guide wire holder, the sheath may have a hook-accommodating lumen which is formed with an inner diameter larger than an outer diameter of the second end portion, the second end portion may be able to be accommodated in the hook-accommodating lumen by retracting the operation wire, and when the second end portion is accommodated in the hook-accommodating lumen, the hook may protrude from the sheath such that the guide wire is capable of being held between the side surface and a portion protruding from the sheath.

In a guide wire holder, the side surface may have a shape in which a part of an outer periphery of a distal end surface of the sheath is cut out and a cut out part extends from the distal end toward a proximal side of the sheath.

In a guide wire holder, the hook and the side surface may be disposed so that the guide wire is held to be able to advance and retract between the hook and the side surface.

In a guide wire holder, the side surface may be formed in a concave shape, and the side surface may form a groove.

In a guide wire holder, in the groove, an opening width of the groove may widen from a bottom portion of the groove toward an outer peripheral surface of the sheath at least at a distal end portion of the sheath.

In a guide wire holder, the side surface which forms the groove may be a curved surface.

In a guide wire holder, the hook and the groove may be disposed so that the guide wire is held to be able to advance and retract between the hook and the groove.

In a guide wire holder, the sheath may have inclined surfaces formed on both sides of the groove, and the inclined surfaces may be inclined from the distal end of the sheath toward a proximal side of the sheath.

In a guide wire holder, when the guide wire is held between the hook and the groove, at least a part of the hook may be located distant from a distal end of the groove.

In a guide wire holder, the side surface may be a flat surface.

A guide wire holder may include a rotation-preventing portion including a restricting portion which is provided in at least a part of the lumen in the direction of the longitudinal axis and in which an opening shape of the lumen in a cross section orthogonal to the longitudinal axis is a non-complete circle, and a restricted portion which is provided in at least a part of the operation wire in an axis direction, has a non-complete circular cross-sectional shape orthogonal to the axis and is able to advance and retract in the restricting portion, the rotation-preventing portion may be configured so that a direction around the axis of the operation wire may be restricted.

In a guide wire holder, the restricting portion may be provided at a distal end portion of the lumen, and a proximal end of the restricting portion may be disposed in the lumen.

In a guide wire holder, the hook may extend to the distal end of the operation wire, the sheath may include a restricting portion which is provided in at least a part of the lumen in the direction of the longitudinal axis and in which an opening shape of the lumen in a cross section orthogonal to the longitudinal axis is a non-complete circle, the hook may have a restricted portion formed by bending a rod-shaped member, and rotation of the operation wire around the axis may be restricted by locking the restricting portion to the restricted portion.

In a guide wire holder, a distal end portion of the sheath may have a pre-curved portion in which the longitudinal axis is curved, a portion of the hook which is able to be accommodated in the lumen may have a first portion which extends further toward a distal side than the restricted portion and a second portion which extends toward a proximal side further than the restricted portion, the first portion may be located further outward with respect to a curve of the pre-curved portion from the second portion, and the second portion may be located further inward with respect to the curve of the pre-curved portion from the first portion.

In a guide wire holder, the distal end of the sheath may have an inclined surface which is inclined from the proximal side toward the distal side in a tapered shape, and the second end portion of the hook may be folded back in a direction intersecting the longitudinal axis of the hook-accommodating lumen.

DETAILED DESCRIPTION OF EXEMPLARY EMBODIMENTS

Figure 1:
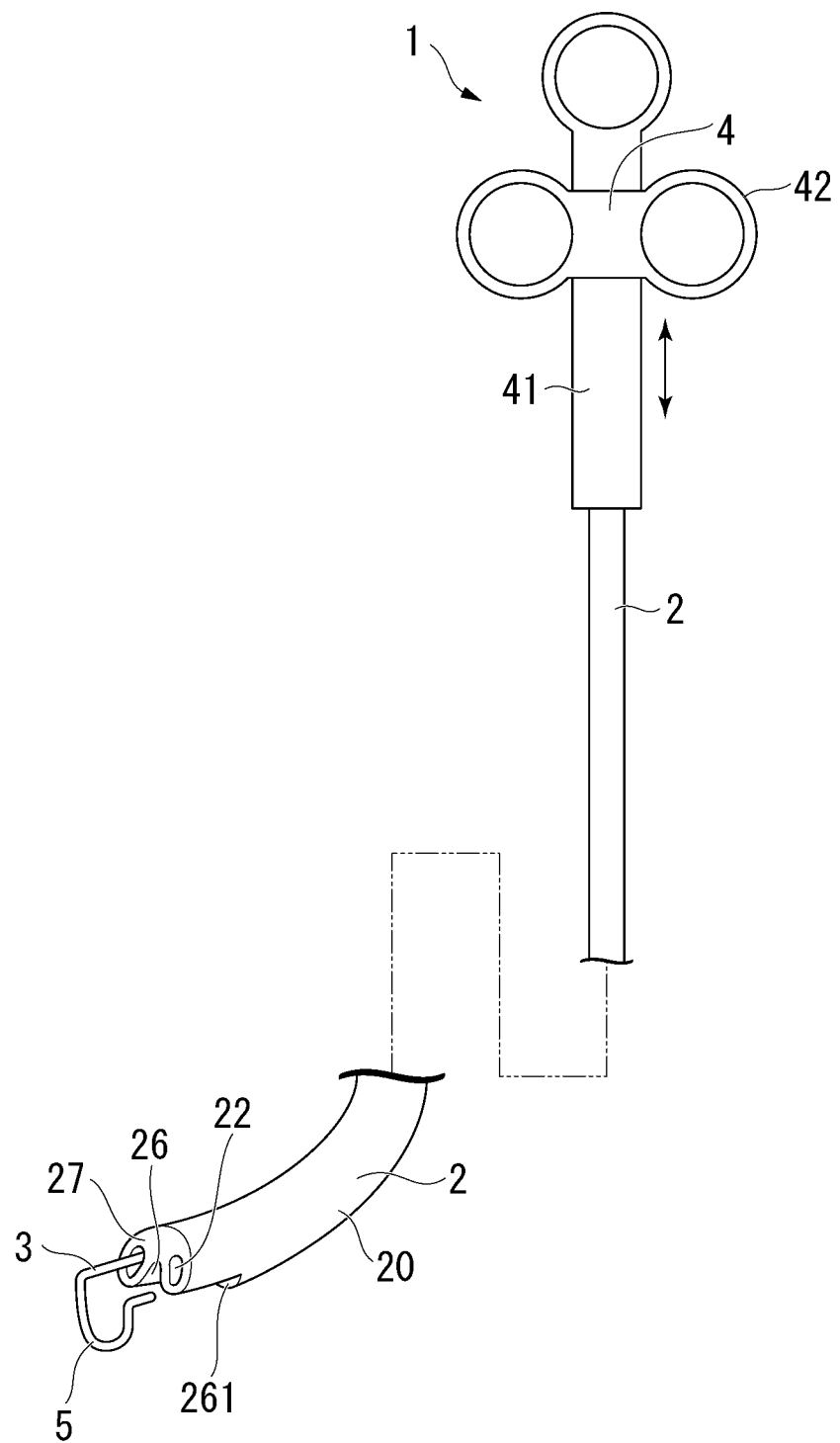
FIG. 1 is an overall view showing a guide wire holder according to an exemplary embodiment.
Figure 2:
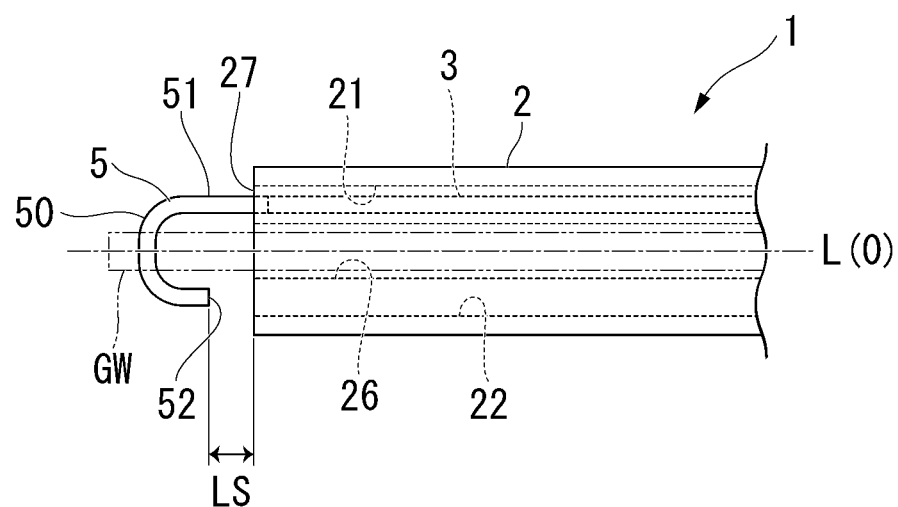
FIG. 2 is a top view showing a distal end portion of the guide wire holder according to an exemplary embodiment.
Figure 3:
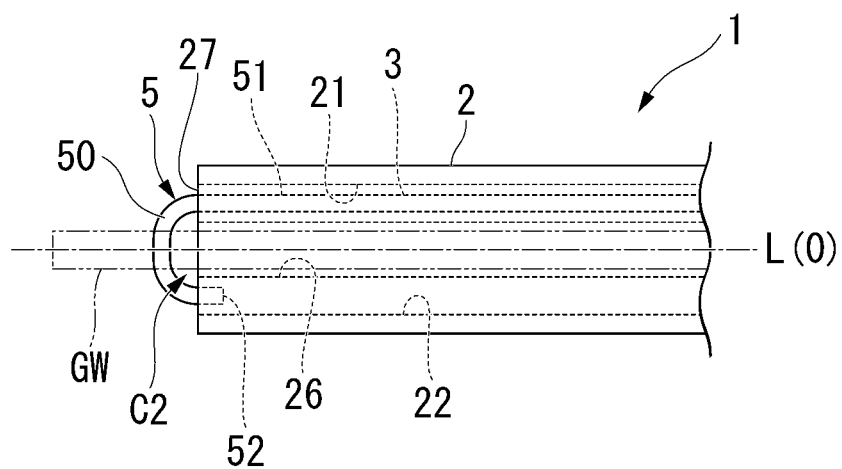
FIG. 3 is a top view showing a distal end portion of the guide wire holder according to an exemplary embodiment.
Figure 4:
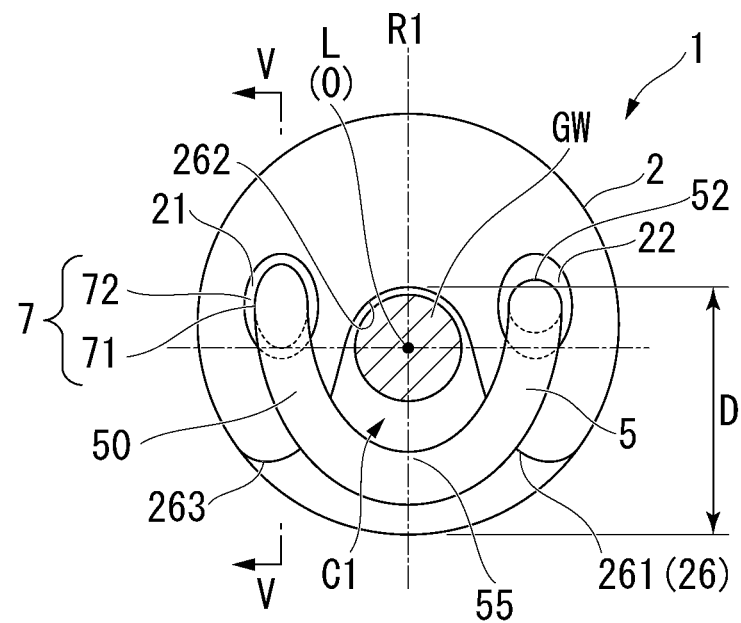
FIG. 4 is a front view of the guide wire holder according to an exemplary embodiment when seen from the distal end side.
Figure 5:
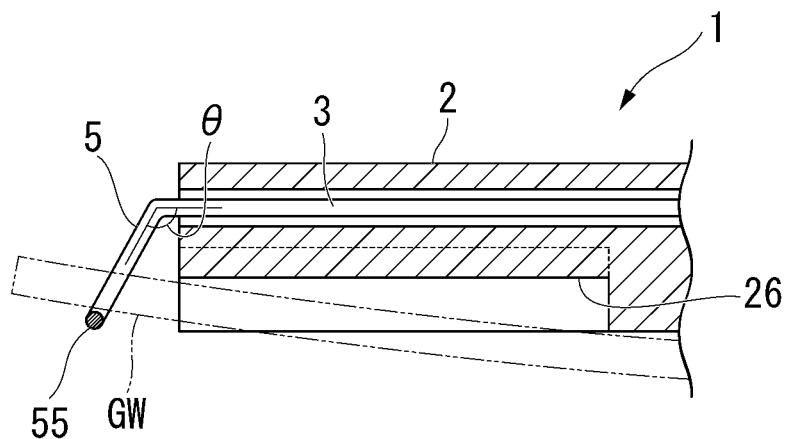
FIG. 5 is a cross-sectional view along line V-V shown in FIG. 4.
Figure 6:
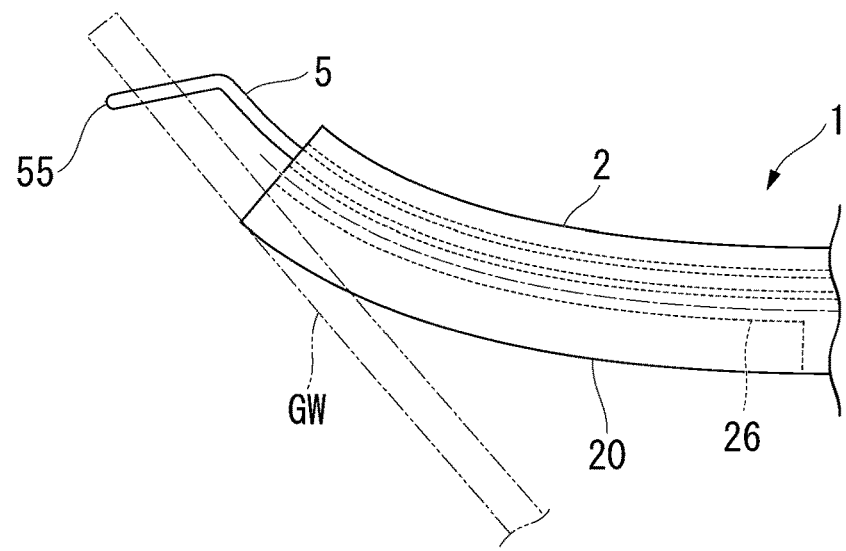
FIG. 6 is a side view showing an aspect of a pre-curved portion of the guide wire holder according to an exemplary embodiment.
Figure 7:
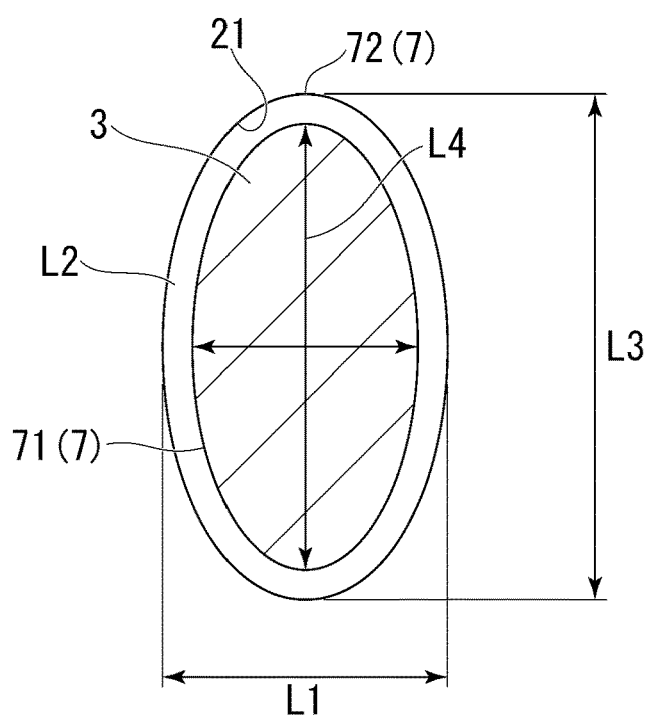
FIG. 7 is a schematic view showing a rotation-preventing structure of the guide wire holder according to an exemplary embodiment.

FIG. 1 is an overall view showing a guide wire holder 1 according to the embodiment. FIG. 2 is a top view showing a distal end portion of the guide wire holder 1. FIG. 3 is a top view showing the distal end portion of the guide wire holder 1 and is a view showing a state in which a hook shown in FIG. 2 is retracted. FIG. 4 is a front view of the guide wire holder 1 when seen from the distal end side. FIG. 5 is a cross-sectional view along line V-V shown in FIG. 4. FIG. 6 is a side view showing an aspect when the guide wire holder 1 is used. FIG. 7 is a view schematically showing a rotation-preventing portion 7 of the guide wire holder 1.

The guide wire holder 1 according to the embodiment is a medical device which is capable of holding a wire, for example, a medical guide wire used by being inserted into the body. The guide wire holder 1 is a treatment tool constituted so that a hook 5 advances and retracts on the distal side of a sheath 2 as an operation wire 3 advances and retracts, and the guide wire located outside the sheath 2 is capable of being captured and held by the hook 5. As shown in FIGS. 1 and 2, the guide wire holder 1 includes the sheath 2, the operation wire 3, the hook 5, and an operation portion 4.

The sheath 2 is a long flexible member. A proximal end portion of the sheath 2 is connected to an operation portion main body 41 of the operation portion 4 which is gripped by an operator. The sheath 2 is inserted into the body through an endoscope insertion portion and has such a length that a distal end portion of the sheath is capable of protruding from the endoscope. As shown in FIGS. 2 to 4, the sheath 2 has a first lumen 21 (a lumen) which extends in a direction of a longitudinal axis L. Further, the sheath 2 has a second lumen (a hook-accommodating lumen) 22 which extends parallel to the first lumen 21. In a front view of the distal end of the sheath 2 seen in a direction along the longitudinal axis L of the sheath 2, the first lumen 21 and the second lumen 22 are formed on both sides of a first diameter line R1 which is a straight line passing through a central axis O of the sheath 2 and orthogonal to the central axis O. The second lumen 22 has an inner diameter larger than an outer diameter of a second end portion 52.

In FIG. 4, although the longitudinal axis L and the central axis O are shown by the same line, the central axis O is an axis which passes through a center of the sheath 2 in a substantially circular cross-sectional shape, and the longitudinal axis L is an axis which extends in a longitudinal direction of the sheath 2.

As shown in FIGS. 1 and 4, a groove 26 is formed in a part of an outer periphery of the sheath 2. The groove 26 is formed in a concave shape at a part of an outer periphery of the sheath 2. The groove 26 is formed to extend from the distal end of the sheath 2 toward the proximal side in the direction of the longitudinal axis L. As shown in FIG. 4, the groove 26 is formed so that a part of the outer periphery of the sheath 2 is recessed from an outer peripheral surface toward the central axis O. The groove 26 has a depth D which is longer than a radius of the sheath 2. In the groove 26, at least at the distal end of the sheath 2, As shown in FIG. 4, in a front view, the groove 26 includes a bottom portion 262 located between the first lumen 21 and the second lumen 22, and a distal end edge (a ridge line) 261 formed in a curved shape in which an opening width of the groove 26 widens from the bottom portion 262 toward the outer peripheral surface of the sheath 2. The bottom portion 262 of the groove 26 is formed in an arc shape in a cross section orthogonal to the central axis O. An edge portion of the groove 26 on an outer peripheral opening portion 263 side on the outer peripheral side of the sheath 2 is formed in a curved shape and has a curved surface. The groove 26 opens on a first diameter line R1. The groove 26 does not necessarily have to have the depth D longer than the radius of the sheath 2 and may have a depth shorter than the radius of the sheath 2.

The groove 26 is formed to extend from the distal end of the sheath 2 toward the proximal side in the direction of the longitudinal axis L. The groove 26 has the same shape as the shape of the distal end edge 261 from a distal end of the groove 26 to the proximal end of the groove 26. The groove 26 may be formed over the entire length of the sheath 2 or may be formed in a region of a predetermined length from the distal end toward the proximal side, for example, only in a portion which protrudes from a distal end of the endoscope insertion portion.

As shown in FIGS. 1 and 6, a pre-curved portion 20 is provided at the distal end portion of the sheath 2. The pre-curved portion 20 is formed by giving a bending tendency in a shape curved in a predetermined direction. In the embodiment, the pre-curved portion 20 has a bending tendency to be bent in a direction of the first diameter line R1. The pre-curved portion 20 is elastically deformed when an external force is applied, but in a natural state in which the external force is released, the pre-curved portion 20 has a restoring force which restores the curved shape given in advance. The groove 26 is formed at a position at which it opens outside the curved shape of the pre-curved portion 20 when the pre-curved portion 20 is restored to the curved shape.

The operation wire 3 is formed of a single wire or a stranded wire made of a metal and is inserted through the first lumen 21 of the sheath 2. A proximal end of the operation wire 3 is fixed to an operation slider 42 of the operation portion 4, and the hook 5 is connected to a distal end of the operation wire 3.

A rotation-preventing portion 7 is provided in the operation wire 3 and the first lumen 21. The rotation-preventing portion 7 prevents the operation wire 3 from rotating about the axis with respect to the first lumen 21. The rotation-preventing portion 7 includes a non-complete circular portion 71 (a restricted portion) provided in the operation wire 3 and a non-complete circular opening portion 72 (a restricting portion) provided in the first lumen 21. The non-complete circular portion 71 is a portion of which a cross-sectional shape orthogonal to an axial direction of the operation wire 3 is elliptical (non-complete circular). The non-complete circular opening portion 72 is an elliptical opening which has an elliptical (non-complete circular) opening shape and is provided to have a predetermined length from the distal end of the first lumen 21 toward the proximal side and a cross-sectional shape thereof orthogonal to the direction of the longitudinal axis L of the sheath 2 is similar to that of the non-complete circular portion 71 of the operation wire 3. As shown in FIG. 7, the non-complete circular opening portion 72 has an opening size which allows the operation wire 3 to advance and retract and in which the non-complete circular portion 71 cannot rotate about the axis of the operation wire 3. The restricting portion and the restricted portion may have a non-complete circular shape and may have an elliptical shape or an oval shape.

As shown in FIG. 7, a dimension L1 of the non-complete circular opening portion 72 in a short side direction of the elliptical shape is larger than a dimension L2 of a cross section of the non-complete circular portion 71 in a short side direction thereof. A dimension L3 of the non-complete circular opening portion 72 in a long side direction of the elliptical shape is larger than the dimension L1 of the non-complete circular portion 71 in the short side direction and a dimension L4 thereof in the long side direction.

Therefore, when the operation wire 3 rotates about its own axis, the non-complete circular portion 71 comes into contact with an inner wall of the non-complete circular opening portion 72, and rotation of the operation wire 3 about the axis is restricted. As a result, the operation wire 3 is constituted to be able to advance and retract in the first lumen 21 while the operation wire 3 is prevented from rotating about the axis with respect to the sheath 2.

The non-complete circular portion 71 of the operation wire 3 is provided in a region at which the operation wire 3 passes through the non-complete circular opening portion 72 of the distal end portion of the first lumen 21 when the operation wire 3 advances and retracts with respect to the sheath 2. In the embodiment, in the operation wire 3, the elliptical non-complete circular portion 71 is provided in a part of the operation wire 3 in the direction of the longitudinal axis, and a cross-sectional shape of a portion other than the non-complete circular portion 71 is substantially completely circular.

As shown in FIGS. 1 to 3, the hook 5 is provided to be continuous with the distal end of the operation wire 3. The hook 5 is formed by bending a wire-shaped member toward the distal end side of the guide wire holder 1 in a convex shape. The hook 5 includes a first end portion 51 which has end portions on both sides of a convex bending region 50 and is connected to the distal end of the operation wire 3, and a second end portion 52 which extends toward the proximal end side of the sheath 2 along the longitudinal axis. The hook 5 may be formed of a single wire made of a metal such as SUS or a nickel titanium alloy.

The hook 5 is provided to protrude from the distal end of the sheath 2. The hook 5 advances and retracts at the distal side of the sheath 2 as the operation wire 3 advances and retracts with respect to the sheath 2.

As shown in FIGS. 4 and 5, in a front view, the hook 5 is formed to be bent in a radial direction (a direction of the first diameter line R1) of the sheath 2 and to the side on which the groove 26 is located. In a side view which is in a direction orthogonal to the direction of the longitudinal axis of the sheath 2 and a direction orthogonal to a bending direction of the pre-curved portion 20, the hook 5 is formed so that the distal end side of the hook 5 is bent toward the groove 26 side at a right angle or an obtuse angle with the distal end part of the guide wire 3. As shown in FIG. 4, in a front view, a protruding end portion 55 of the curved portion at the distal end of the hook 5 is located outward from the bottom portion 262 of the groove 26 in the radial direction of the sheath 2. That is, the hook 5 is bent toward the groove 26 in the direction of the first diameter line R1 between the first end portion 51 and the second end portion 52 and the protruding end portion 55.

In a front view, the hook 5 intersects the distal end edge 261 of the groove 26, and a closed region C1 closed by the hook 5 and the distal end edge 261 is formed. As shown in FIG. 3, in a first side view (a top view) seen in a direction along the first diameter line R1, when the hook 5 is disposed at a retracted position, the second end portion 52 is accommodated in the distal end of the sheath 2 to form a closed region C2 between the hook 5 and the distal end of the sheath 2.

As shown in FIG. 1, the operation portion 4 is provided on the proximal end side of the guide wire holder 1 and is connected to the proximal end of the sheath 2. The operation portion 4 includes an operation portion main body 41 and the operation slider 42. The operation portion main body 41 is connected to the proximal end of the sheath 2. The operation slider 42 is slidably mounted on the operation portion main body 41. The operation portion main body 41 has a hollow portion, and a slit (not shown) which is allowed to communicate with the hollow portion and the outside and extends along the longitudinal axis L is formed. A part of the operation slider 42 is inserted through the slit, and the operation slider 42 is connected to the proximal end portion of the operation wire 3 in the hollow portion. When the operation slider 42 is advanced and retracted with respect to the operation portion main body 41 in the direction of the longitudinal axis L of the sheath 2, the operation wire 3 advances and retracts with respect to the sheath 2, and the hook 5 is capable of advancing and retracting on the distal end side of the sheath 2 according to the advancing and retracting of the operation wire 3.

When the operation slider 42 is advanced with respect to the operation portion main body 41, the operation wire 3 advances in the first lumen 21, and the hook 5 advances on the distal side of the sheath 2. When the operation slider 42 is advanced furthest to the distal side in a movable range of the operation slider 42, the hook 5 is disposed at the most advanced position with respect to the sheath 2. As shown in FIG. 2, the second end portion 52 of the hook 5 is separated from the distal end of the sheath 2 in the advanced position. Specifically, a separation distance LS (refer to FIG. 2) between the second end portion 52 and the distal end of the sheath 2 in the advanced position is longer than a diameter of a guide wire GW which will be described later.

The second end portion 52 is capable of being accommodated in the second lumen 22 by retracting the operation wire 3. When the operation slider 42 is retracted furthest to the proximal side in the movable range of the operation slider 42, as shown in FIG. 3, the hook 5 is disposed at the most retracted position with respect to the sheath 2, and the second end portion 52 enters a distal end opening of the second lumen 22 and is accommodated therein.

Since the rotation of the operation wire 3 around the axis is prevented by the rotation-preventing portion 7, the hook 5 advances and retracts while a relative position around the central axis O of the sheath 2 is maintained. Therefore, the second end portion 52 is capable of reliably entering the distal end opening of the second lumen 22 at the retracted position of the hook 5.

Figure 8:
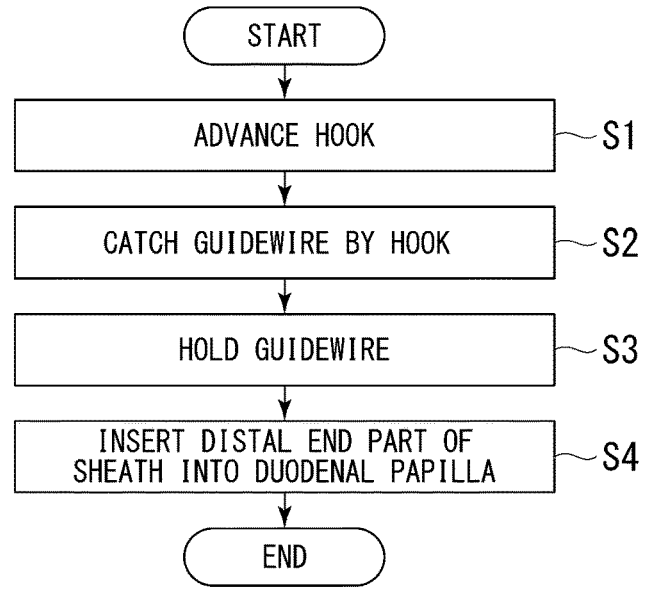
FIG. 8 is a flowchart showing a method for inserting the guide wire holder according to an exemplary embodiment.
Figure 9:
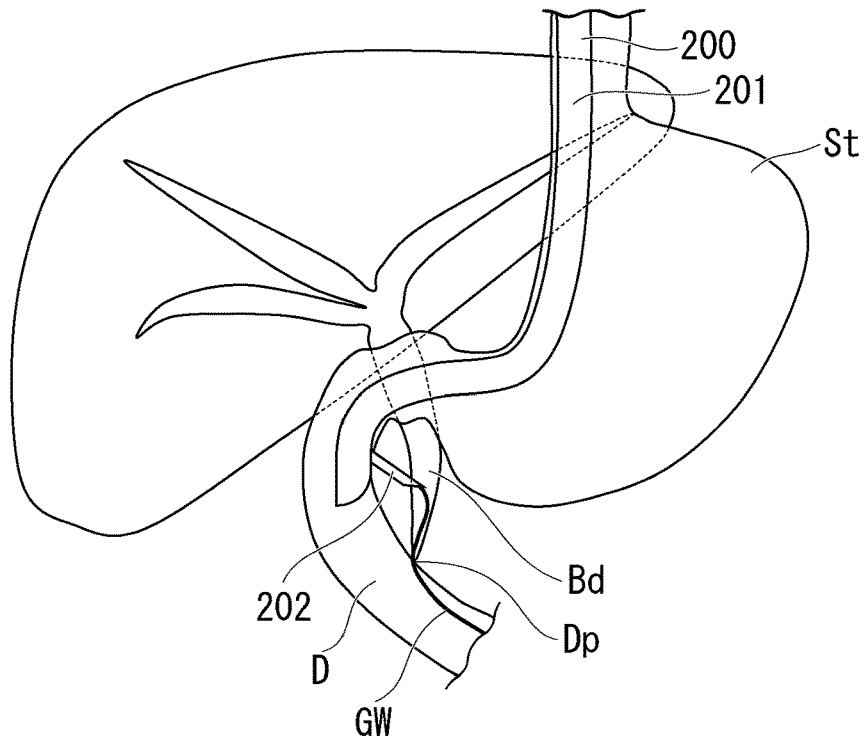
FIG. 9 is a schematic view showing an aspect when the guide wire holder according to an exemplary embodiment.
Figure 10:
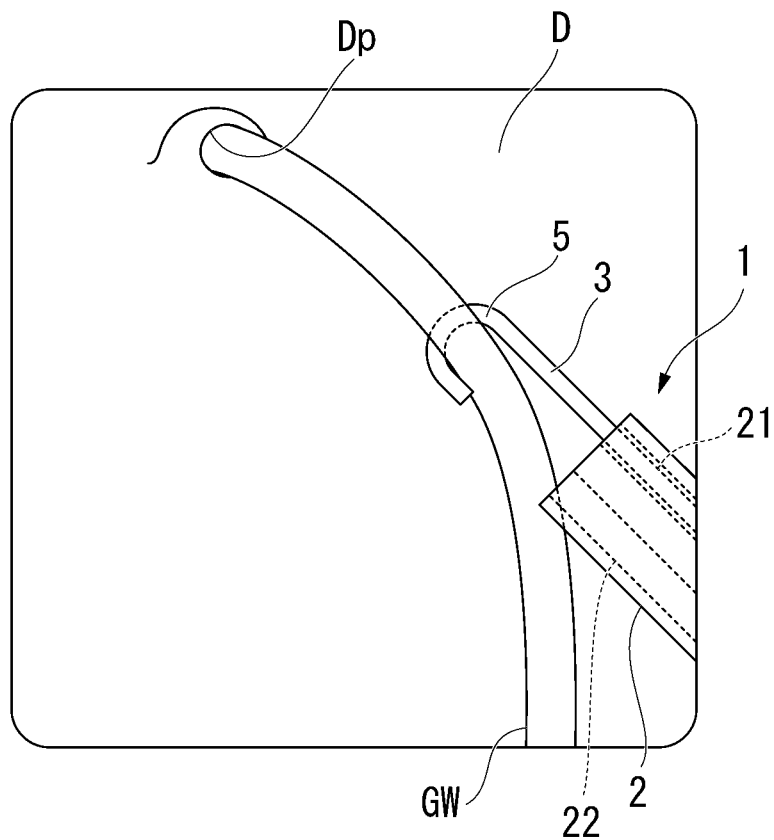
FIG. 10 is a schematic view showing an endoscopic image in an example in which a procedure is performed by a rendezvous method using the guide wire holder according to an exemplary embodiment.
Figure 11:
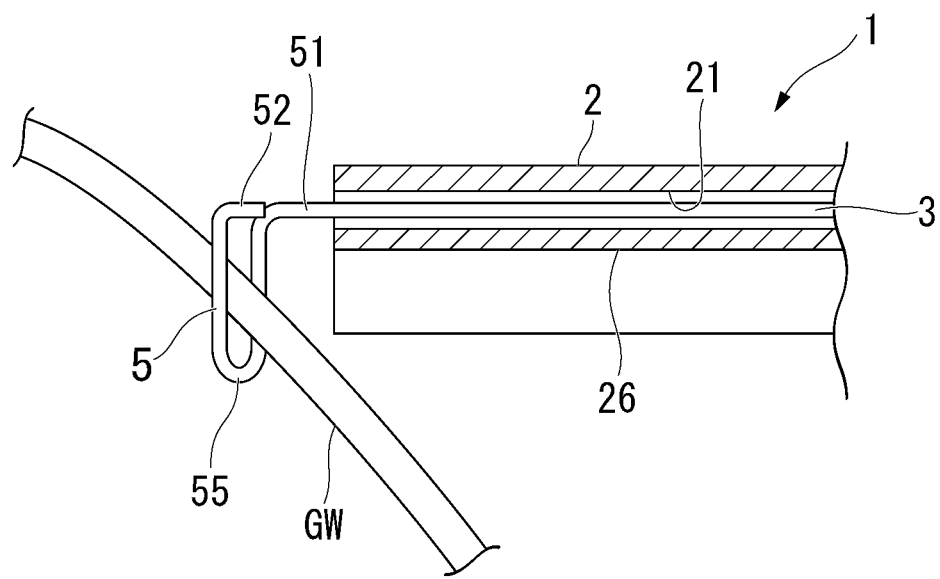
FIG. 11 is a schematic view showing an aspect when the guide wire holder according to an exemplary embodiment is used.
Figure 12:
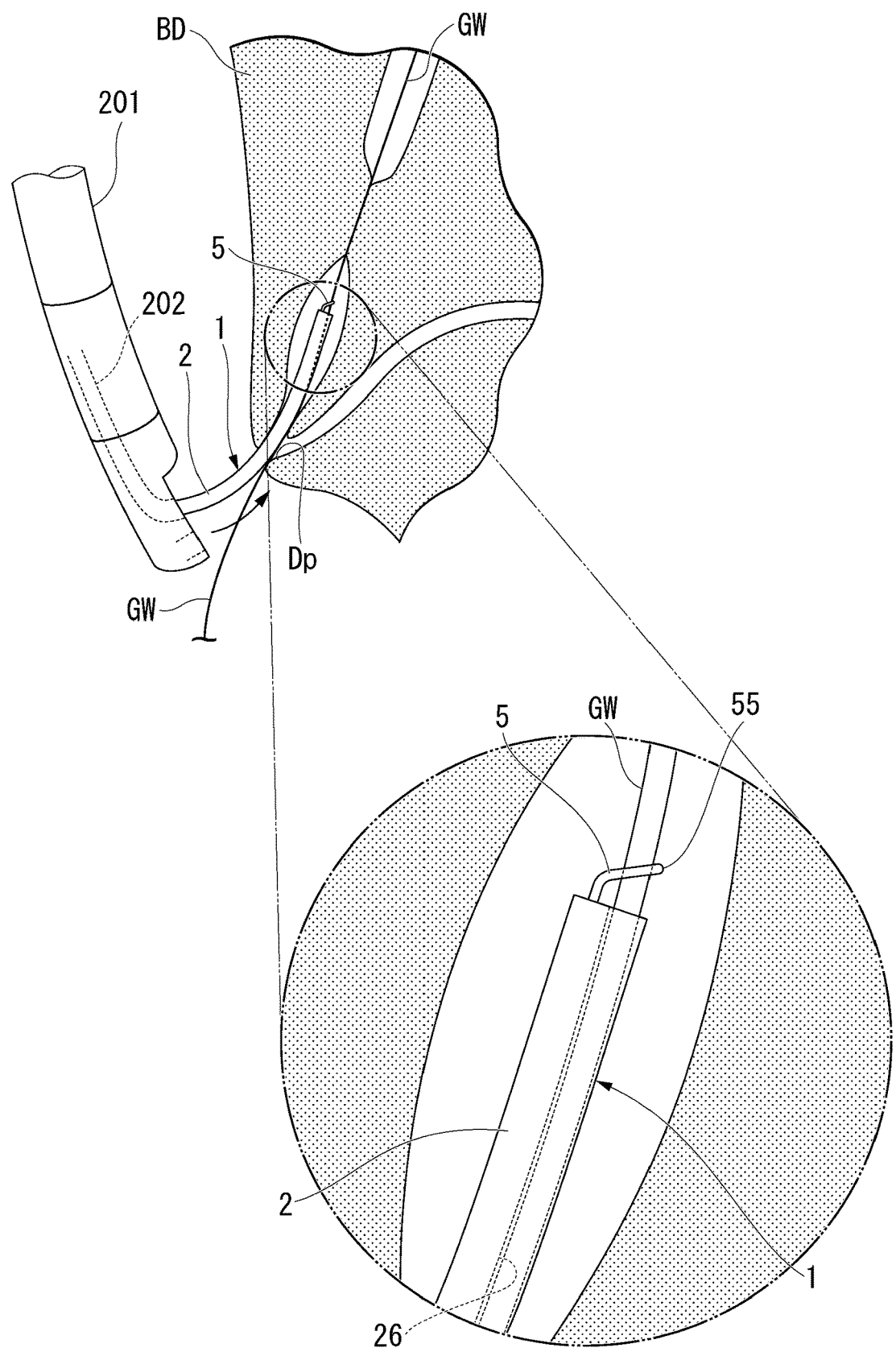
FIG. 12 is a schematic view showing an endoscopic image in an example in which a procedure is performed by a rendezvous method using the guide wire holder according to an exemplary embodiment.

Next, a usage aspect of the guide wire holder 1 and a method for inserting the guide wire holder will be described. In the following, a method for introducing the guide wire holder 1 into a hollow organ, for example, the bile duct by the rendezvous method will be described as an example. FIG. 8 is a flowchart showing the method for inserting the guide wire holder according to the embodiment. FIGS. 9 to 11 are schematic views showing an aspect when the guide wire holder 1 is used. FIG. 12 is a schematic view showing an example in which a procedure is performed by the rendezvous method using the guide wire holder 1.

First, a first guide wire GW (the guide wire) is placed in a duodenum D. Specifically, as shown in FIG. 9, an endoscope insertion portion 201 of an ultrasonic endoscope 200 is inserted from a mouth of a patient into a stomach St or the duodenum D, and an access needle 202 which is inserted through the endoscope insertion portion 201 and protrudes from the distal end of the endoscope insertion portion 201 is punctured into a bile duct Bd. Then, the first guide wire GW is inserted into the endoscope insertion portion 201, and the first guide wire GW is inserted into the bile duct Bd via the access needle 202. The first guide wire GW inserted into the bile duct Bd is pushed forward, and the distal end of the first guide wire GW protrudes from a duodenal papilla Dp into the duodenum D. Normally, the distal end of the first guide wire GW which protrudes from the duodenal papilla Dp is made to extend along the lumen of the duodenum D by advancing the first guide wire GW toward the duodenal papilla Dp. After that, the ultrasonic endoscope 200 is removed with the first guide wire GW left inside the body, and the distal end of the first guide wire GW is placed in the duodenum D. At this time, a proximal end part of the first guide wire GW is outside the patient's body.

Next, the endoscope insertion portion 201 (refer to FIG. 12) of a duodenoscope (not shown) is inserted from the patient's mouth to the duodenum D. Then, the guide wire holder 1 is inserted into the endoscope insertion portion 201, and the distal end portion of the sheath 2 protrudes from the distal end of the endoscope insertion portion 201. At this time, the distal end portion of the sheath 2 is raised by an elevator (not shown) provided at a distal end portion of a treatment tool channel 203 of the endoscope insertion portion 201. When the distal end portion of the sheath 2 protrudes from the treatment tool channel 203 of the endoscope insertion portion 201, the pre-curved portion 20 is restored to a predetermined curved shape. Therefore, the distal end portion of the sheath 2 is capable of being easily arranged to be displayed in an endoscopic image, and the sheath 2 is also capable of being guided in a direction in which the hook 5 easily hooks the guide wire GW. The guide wire GW is capable of being easily inserted into the groove 26. Since the second end portion 52 of the hook 5 is located in the central part of the endoscopic image, the second end portion 52 is capable of being seen closer to a center of the endoscopic image than the first guide wire GW. As a result, in the endoscopic image, a gap between the second end portion 52 and the sheath 2 is prevented from being blocked by the first guide wire GW, and the hook 5 is capable of smoothly hooking the first guide wire GW.

As shown in FIG. 10, an operator operates the operation portion 4 while checking the endoscopic image obtained by the duodenoscope. Specifically, the endoscope insertion portion 201 is disposed so that the first guide wire GW which protrudes from the duodenal papilla Dp toward the inside of the duodenum D is displayed in the endoscopic image, and in this state, the sheath 2 protrudes from the endoscope insertion portion 201 to bring the sheath 2 close to the first guide wire GW. As shown in FIG. 10, the distal end portion of the sheath 2 is imaged to protrude from the lower right side of the endoscopic image. When the sheath 2 is caused to protrude from the endoscope, the sheath 2 is disposed at a position in which the gap between the second end portion 52 of the hook 5 and the distal end of the sheath 2 is capable of being visually recognized in the endoscopic image. That is, the second end portion 52 is displayed closer to the proximal side than the first end portion 51 on the endoscopic image.

Then, the operation slider 42 is advanced toward the distal side, the operation wire 3 is advanced with respect to the sheath 2, and the hook 5 is advanced to the advanced position with respect to the sheath 2 (a hook advance step S1).

As shown in FIGS. 10 and 11, the operator inserts the first guide wire GW into the gap between the second end portion 52 of the hook 5 and the distal end of the sheath 2 while checking the endoscopic image. Then, the first guide wire GW is hooked by the hook 5 (a locking step S2).

The guide wire GW which protrudes from the duodenal papilla Dp runs from the upper side to the lower side in the endoscopic image, and the vicinity of the distal end of the endoscope is displayed on the lower side of the endoscopic image. On the other hand, when the pre-curved portion 20 passes through a forceps-elevator 100, the outside of the curve of the pre-curved portion 20 faces the forceps-elevator 100 (refer to FIG. 26). Therefore, since the groove 26 is formed on the outside of the curve of the pre-curved portion 20, the groove 26 is located below the endoscopic image when the pre-curved portion 20 protrudes from the endoscope. As a result, it becomes easy to accommodate the guide wire GW in the groove 26 of the sheath 2. Since a vector of a force pushing the sheath 2 is easily converted in a long axis direction of the guide wire GW, the distal end portion of the sheath 2 is likely to follow the guide wire GW.

Next, the operator retracts the operation slider 42 toward the proximal side, retracts the operation wire 3 with respect to the sheath 2 and places the hook 5 in the retracted position. The first guide wire GW is capable of being brought close to the distal end edge of the groove 26 by retracting the hook 5 to the retracted position. In the retracted position, the second end portion 52 of the hook 5 is inserted into the second lumen 22, and the first guide wire GW is disposed and captured in the closed regions C1 and C2 between the hook 5 and the sheath 2 (a guide wire holding step S3).

In the state in which the hook 5 is retracted to the retracted position, the guide wire GW is inserted into the groove 26. At this time, the guide wire GW is captured and held by the groove 26 and the hook 5 in a state in which the guide wire GW is arranged from the groove 26 toward the proximal side of the sheath 2 along the direction of the longitudinal axis L.

Next, in a state in which the guide wire GW is held between the hook 5 and the groove 26, the distal end portion of the sheath 2 is inserted into the duodenal papilla Dp along the guide wire GW while an inner wall surface of the groove 26 is pressed against the guide wire GW (a sheath insertion step S4). The operator pushes the operation portion 4 and inserts the distal end portion of the sheath 2 into the duodenal papilla Dp as shown in FIG. 12. Since the first guide wire GW passes through the bile duct Bd and extends to the duodenum D via the duodenal papilla Dp in advance, when the guide wire holder 1 is pushed in, the sheath 2 advances along the first guide wire GW and reaches the inside of the bile duct Bd.

Since the closed regions C1 and C2 are sufficiently larger than the diameter of the first guide wire GW, the sheath 2 and the hook 5 do not generate a large frictional resistance with the first guide wire GW. Therefore, the sheath 2 is capable of being smoothly advanced and retracted along the first guide wire GW. Further, when the sheath 2 is advanced into the duodenal papilla Dp, the first guide wire GW is disposed in the groove 26 of the sheath 2 in the direction of the longitudinal axis L of the sheath 2, and the guide wire GW is also held between the hook 5 and the groove 26. As a result, a state in which the first guide wire GW is disposed along the longitudinal axis L of the sheath 2 is maintained. At this time, at least a part of the hook 5 is located distant from the distal end of the groove 26. Further, the first guide wire GW is held along the longitudinal axis L at a position closer to the central axis O of the sheath 2, and as described above, the sheath 2 and the hook 5 smoothly advance and retract with respect to the first guide wire GW. Therefore, the sheath 2 and the hook 5 is capable of being easily inserted into the bile duct Bd. In this way, the insertion of the first guide wire GW into the bile duct Bd is completed.

After the insertion of the first guide wire GW into the bile duct Bd is completed, an intended treatment is performed. As a specific example, a second guide wire different from the first guide wire GW is inserted into another lumen (not shown) of the sheath 2 or the second lumen 22, and the second guide wire is inserted into the duodenal papilla Dp. Then, the first guide wire GW and the guide wire holder 1 are removed from the endoscope insertion portion 201.

After that, another endoscopic treatment tool is inserted into the duodenoscope and is inserted into the duodenum along the second guide wire, and then a treatment in the duodenum is performed. Examples of treatments performed by another endoscopic treatment tool include injection of a contrast medium, calculus removal, and a placement of a stent, and the like.

According to the guide wire holder 1 of the embodiment, since the hook 5 which protrudes from the distal end of the sheath 2 and is capable of advancing and retracting with respect to the sheath 2 is provided, the guide wire GW is capable of being held by the hook 5. According to the guide wire holder 1 of the embodiment, the guide wire GW is capable of being easily hooked by the hook 5 by disposing the hook 5 at the advanced position. When the guide wire GW is hooked by the hook 5, the gap formed between the second end portion 52 and the distal end of the sheath 2 is capable of being visually recognized in the endoscopic image, and thus the guide wire GW is easily hooked by the hook 5. Since the separation distance LS between the second end portion 52 and the distal end of the sheath 2 at the advanced position of the hook 5 is larger than the outer diameter of the guide wire GW, the guide wire GW is capable of being easily hooked by the hook 5. Then, the guide wire GW is capable of being prevented from coming off from the hook 5 by disposing the hook 5 in the retracted position.

Since the closed regions C1 and C2 formed by the hook 5 and the distal end of the sheath 2 are larger than the outer diameter of the guide wire GW, the guide wire GW captured in the closed regions C1 and C2 are capable of smoothly advancing and retract in the closed regions C1 and C2. As a result, when the distal end portion of the guide wire holder 1 is inserted into the duodenum, the sheath 2 is capable of being easily advanced along the guide wire GW.

According to the guide wire holder 1 of the embodiment, the rotation of the operation wire 3 around its own axis is restricted by the rotation-preventing portion 7. As a result, when the hook 5 advances and retracts, the second end portion 52 of the hook 5 is prevented from rotating around the central axis O of the sheath 2, and the second end portion 52 is capable of being reliably inserted into the second lumen 22 when the hook 5 retracts.

Since the guide wire holder 1 according to the embodiment includes the groove 26 formed along the longitudinal axis L on the outer periphery of the sheath 2, when the inner wall surface of the groove 26 is pressed against the guide wire GW located outside the sheath 2, the guide wire GW is capable of being easily inserted into the groove 26.

According to the guide wire holder 1 of the embodiment, in a front view seen in the direction along the longitudinal axis L, the hook 5 intersects the distal end edge 261 of the groove 26, and the hook 5 and the distal end edge 261 form the closed region C1. Therefore, in a state in which the hook 5 is disposed at the retracted position, the guide wire GW located outside the sheath 2 is capable of being captured in the groove 26 and held in the closed region C1. As a result, the guide wire GW is capable of being easily hooked by the hook 5 by the advancing and retracting operation of the operation wire 3, and the guide wire GW is capable of being surrounded and held between the hook 5 and the distal end edge 261 of the groove 26. Therefore, when the sheath 2 is inserted into the duodenal papilla Dp, the hook 5 does not come off from the guide wire GW, and the sheath 2 is capable of being inserted into the duodenal papilla Dp in a stable state.

According to the guide wire holder 1 of the embodiment, since the guide wire GW is inserted and held in the groove 26, the guide wire GW is capable of being held near the central axis O of the sheath 2. Therefore, the guide wire GW is capable of being held by a simple operation, and the sheath 2 is capable of being smoothly advanced along the guide wire GW in the lumen organ. Furthermore, since the guide wire GW is captured and held along the groove 26, when the sheath 2 is inserted into the duodenal papilla Dp, a diameter of a portion including the sheath 2 and the guide wire GW is capable of being curbed, and the sheath 2 is capable of being easily inserted into the duodenal papilla Dp.

Since the guide wire holder 1 according to the embodiment includes the pre-curved portion 20 in the sheath 2, and the groove 26 is formed to open outside a restored curved shape of the pre-curved portion 20, the guide wire GW is capable of being easily inserted into the groove 26. Also, the pre-curved portion 20 is not an essential component, and the guide wire holder 1 is capable of smoothly inserting the guide wire GW into the groove 26 even when the sheath 2 does not include the pre-curved portion 20.

The guide wire holder is not limited to the example of the above-described embodiment. For example, modified examples shown in FIGS. 13 to 34 is capable of being cited. In the following description, the same components as those already described will be designated by the same reference numerals, and duplicate description thereof will be omitted.

First Modified Example

Figure 13:
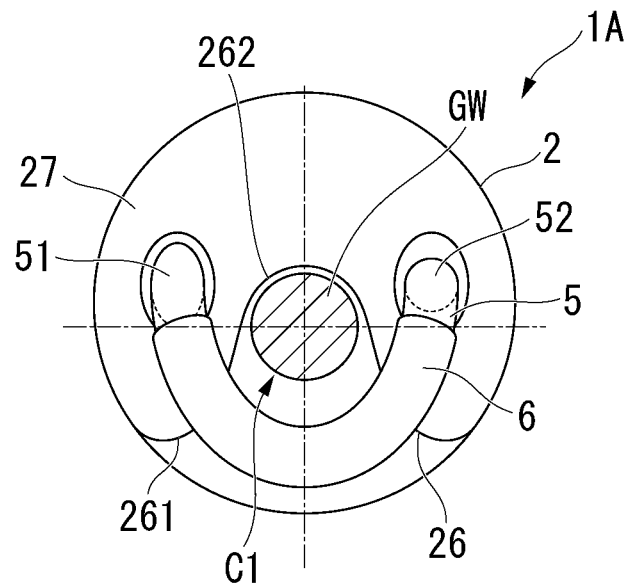
FIG. 13 is a front view of a guide wire holder of an exemplary embodiment when seen from the distal end side.

FIG. 13 is a front view of a guide wire holder 1A according to a first modified example. As shown in FIG. 13, a resin cover member 6 may be provided on the hook 5. The frictional resistance between the guide wire GW and the hook 5 is capable of being reduced by providing the resin cover member 6 on a portion of the hook 5 which protrudes from the sheath 2. As a result, when the sheath 2 is pushed along the guide wire GW, the sheath 2 is capable of being pushed in easily. The cover member 6 is not an essential component. For example, in addition to the resin cover, the hook may be coated with a lubricant or PTFE coating. In addition, when the closed regions C1 and C2 are sufficiently wide with respect to the diameter of the guide wire GW, contact between the guide wire GW and the hook 5 is curbed, and thus the cover member 6 is unnecessary.

Second Modified Example

Figure 14:
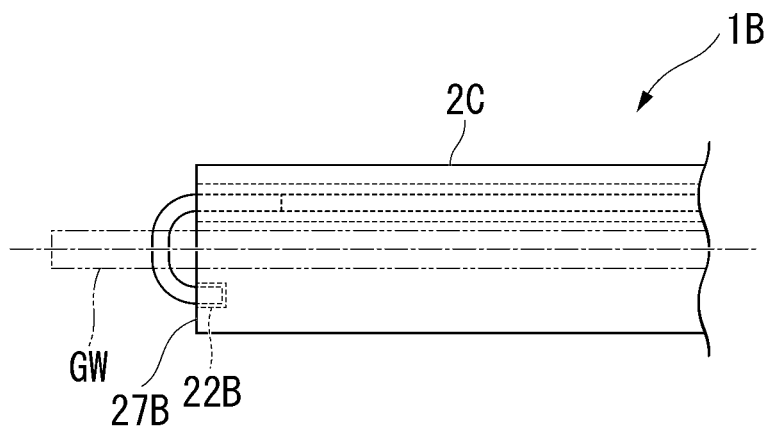
FIG. 14 is a front view of a guide wire holder of an exemplary embodiment when seen from the distal end side.

FIG. 14 is a top view of a guide wire holder 1B of a second modified example. The second modified example shown in FIG. 14 is different from the above-described embodiment in the constitution of the hook-accommodating lumen of the second end portion 52 of the sheath 2. In the second modified example, a bottomed concave portion 22B which opens to a distal end surface 27B of the sheath 2 is formed in the sheath 2. The concave portion 22B serves as the hook-accommodating lumen of the second end portion 52 when the hook 5 is located at the retracted position. In the above-described embodiment, an example in which the second lumen 22 in which a duct is formed over the entire length of the sheath 2 and through which a contrast medium or another wire is capable of being inserted is used as the hook-accommodating lumen is provided. However, for the purpose of accommodating the second end portion 52 of the hook 5, instead of the second lumen 22 formed over the entire length, a concave portion may be formed only at the distal end of the sheath 2 and the second end portion 52 may be accommodated in the concave portion. Since the hook-accommodating lumen is provided separately from the second lumen 22, the second lumen 22 is capable of being used for other purposes in a state in which the hook 5 is held in the retracted position. For example, the second guide wire is capable of being supplied from the second lumen 22 in the state in which the hook 5 is held in the retracted position.

Third Modified Example

Figure 15:
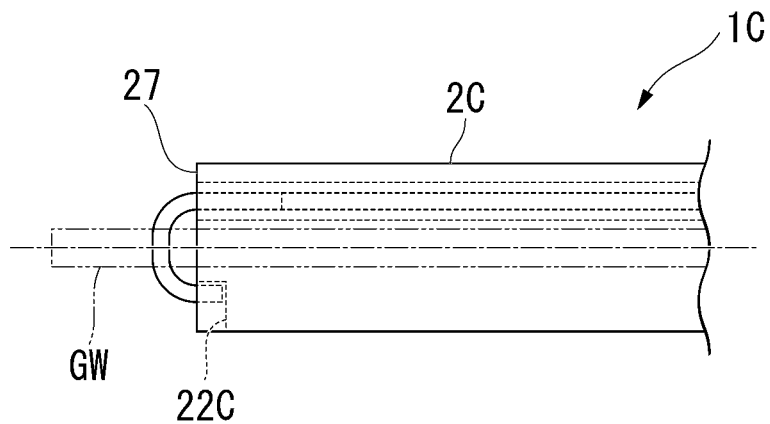
FIG. 15 is a front view of a guide wire holder of an exemplary embodiment when seen from the distal end side.
Figure 16:
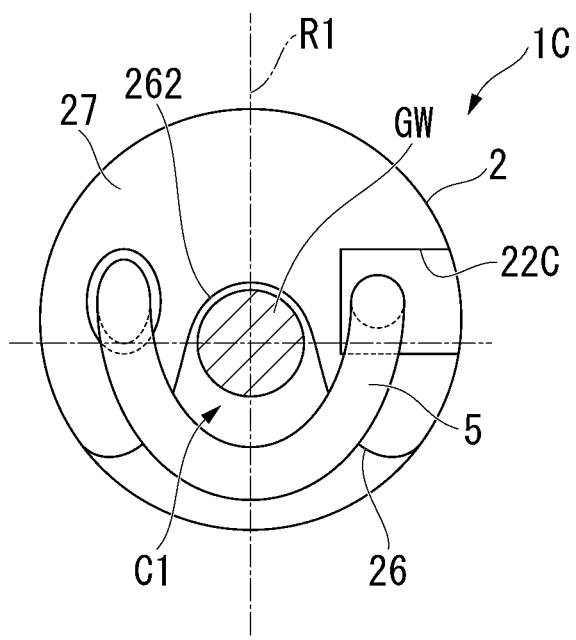
FIG. 16 is a front view of the guide wire holder shown in FIG. 15 when seen from the distal end side.

FIG. 15 is a top view of a guide wire holder 1C of a third modified example. FIG. 16 is a front view of the guide wire holder 1C of the third modified example. The third modified example shown in FIGS. 15 and 16 is different from the concave portion 22B of the second modified example in a shape. A concave portion 22C of the third modified example is formed to be recessed in a region including a boundary portion between the distal end surface 27C of the sheath 2 and the outer peripheral surface thereof. Even when the hook-accommodating lumen which is capable of accommodating the second end portion 52 has such a constitution, the second end portion 52 is capable of being easily accommodated.

Fourth Modified Example

Figure 17:
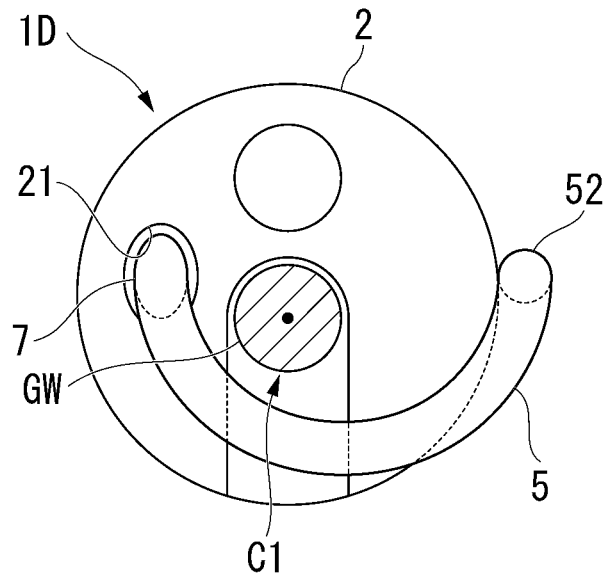
FIG. 17 is a front view of a guide wire holder of an exemplary embodiment when seen from the distal end side.

FIG. 17 is a front view of a guide wire holder 1D of a fourth modified example. This modified example is an example without the hook-accommodating lumen. As shown in FIG. 17, when the hook 5 is disposed at the retracted position, the second end portion 52 may be located outward from the outer peripheral surface of the distal end of the sheath 2 to be disposed close thereto. Also in such a modified example, when the hook 5 is retracted to the retracted position, the second end portion 52 is capable of being located closer to the proximal end side than the distal end of the sheath 2, and the closed region C1 is capable of being formed in a front view. When the hook-accommodating lumen is not provided and the hook 5 is disposed in the retracted position, the second end portion 52 may be in contact with or disposed close to the distal end of the sheath 2. When the second end portion 52 is disposed close to the distal end of the sheath 2 at the retracted position of the hook 5, and the separation distance LS between the second end portion 52 of the hook 5 and the distal end of the sheath 2 is smaller than the outer diameter of the guide wire, the guide wire GW is capable of being held.

Fifth Modified Example

Figure 18:
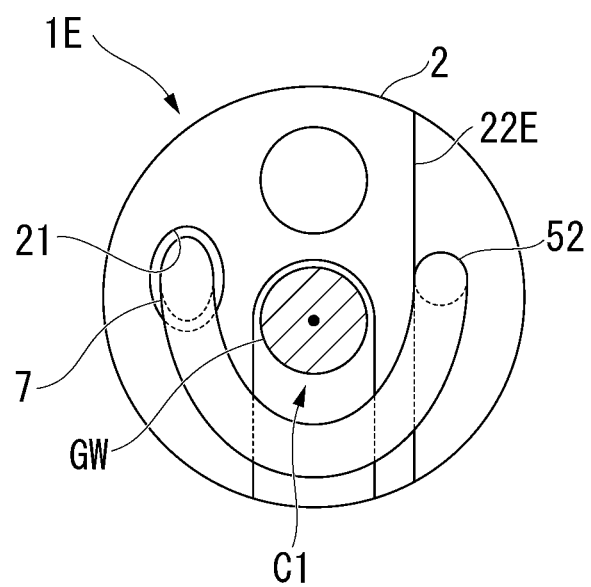
FIG. 18 is a front view of a guide wire holder of an exemplary embodiment when seen from the distal end side.

FIG. 18 is a front view of a guide wire holder 1E according to a fifth modified example. In this modified example, as shown in FIG. 18, an outer surface 22E which is substantially parallel to the longitudinal axis of the sheath 2 may be formed by D-cutting (cutting into a D-shape) a position of a distal end portion of a sheath 2E in which the second end portion 52 advances and retracts without forming the hook-accommodating lumen. Also in such a modified example, when the hook 5 is retracted to the retracted position, the second end portion 52 is capable of being located closer to the proximal end side than the distal end of the sheath 2, and the closed region C1 is capable of being formed in a front view.

Sixth Modified Example

Figure 19:
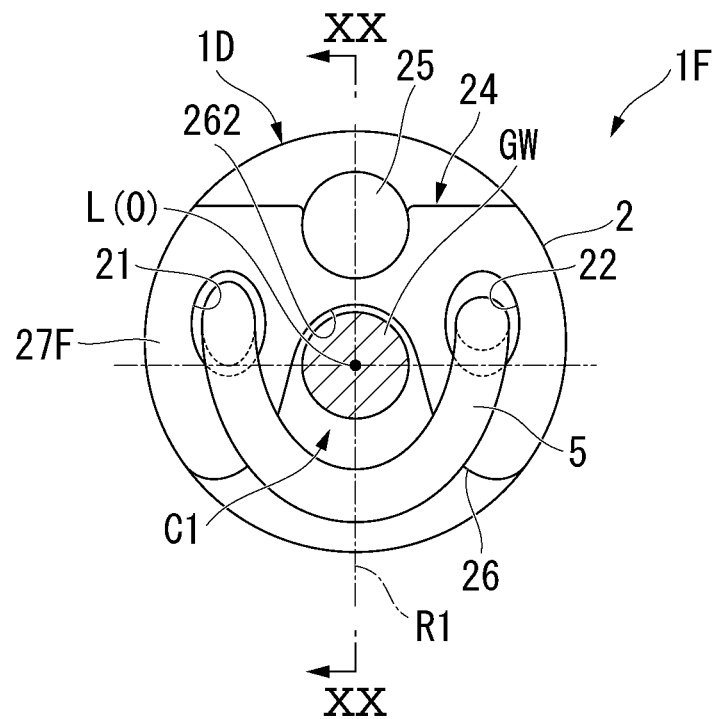
FIG. 19 is a front view of a guide wire holder of an exemplary embodiment when seen from the distal end.
Figure 20:
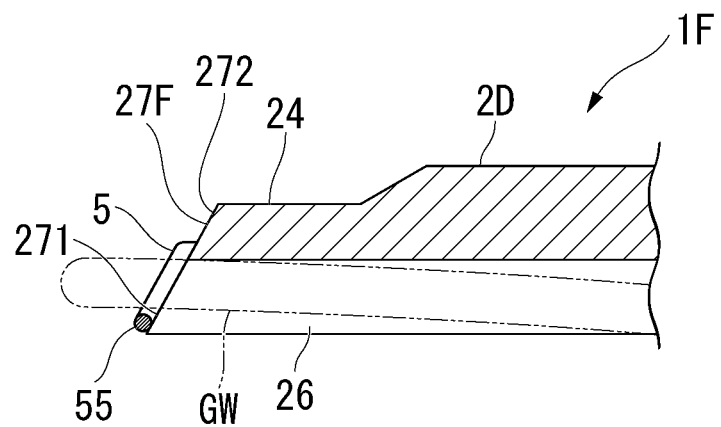
FIG. 20 is a cross-sectional view along line XX-XX in FIG. 19.

FIG. 19 is a front view of a guide wire holder 1F of a sixth modified example. FIG. 20 is a cross-sectional view along line XVII-XVII in FIG. 19. The sixth modified example shown in FIGS. 19 and 20 is different from the sheath 2 of the above embodiment in a shape and constitution of a distal end portion of a sheath 2F.

As shown in FIGS. 19 and 20, in this modified example, a cutout portion (a step) 24 is provided in a part of the distal end portion of the sheath 2F, and a dimension of the distal end portion of the sheath 2F is smaller than the proximal side. The sheath 2F is capable of being more easily inserted into the duodenal papilla Dp by thus reducing a size of the distal end portion of the sheath 2F.

As shown in FIG. 19, in the sheath 2F of the modified example, the groove 26 and a contrast lumen 25 are arranged and provided in the direction of the first diameter line R1, and the cutout portion 24 is provided at a distal end portion of the contrast lumen 25. Therefore, a dimension of the cutout portion 24 in the direction of the longitudinal axis L is set to be equal to or less than a length in which the sheath 2F is inserted into the bile duct. This is because when the cutout portion 24 is longer than the length in which the sheath 2DF is inserted into the bile duct, a distal end opening of the contrast lumen is not inserted into the bile duct and the contrast medium cannot be injected into the bile duct. Further, preferably, the cutout portion 24 in the direction of the first diameter line R1 is formed to be cut out such that the first lumen 21 and the second lumen 22 do not communicate with the outside of the sheath 2F.

Further, in the above-described embodiment, although the distal end surface 27 of the sheath 2 is formed by a surface of the sheath 2 orthogonal to the longitudinal axis L, a distal end surface 27F of the sheath 2F may be formed to be inclined with respect to the central axis O, as shown in FIG. 20. Specifically, the distal end surface 27F of the sheath 2F may be formed to be inclined such that a portion 271 on the groove 26 side may be located on the distal end side and a portion 272 on the cutout portion 24 side may be located on the proximal side, and an inclination angle of the distal end surface 27F of the sheath 2F may be substantially parallel to an inclination angle of the hook 5 in a radial direction. In this way, in the case in which the groove 26 side of the sheath 2F is located on the distal end side, and the distal end surface 27F of the sheath 2F is inclined to be substantially parallel to the hook 5, the distal end of the sheath 2F is capable of being smoothly inserted along the guide wire GW held at the hook 5 and the distal end of the sheath 2F when a sheath 2D is inserted into the duodenal papilla Dp.

The mode in which the dimension of the distal end portion of the sheath 2F is made smaller than that of the proximal end side is not limited to the form shown in this modified example. For example, the distal end portion of the sheath may be tapered so that the distal end side becomes thinner over the entire circumference.

Seventh Modified Example

Figure 21:
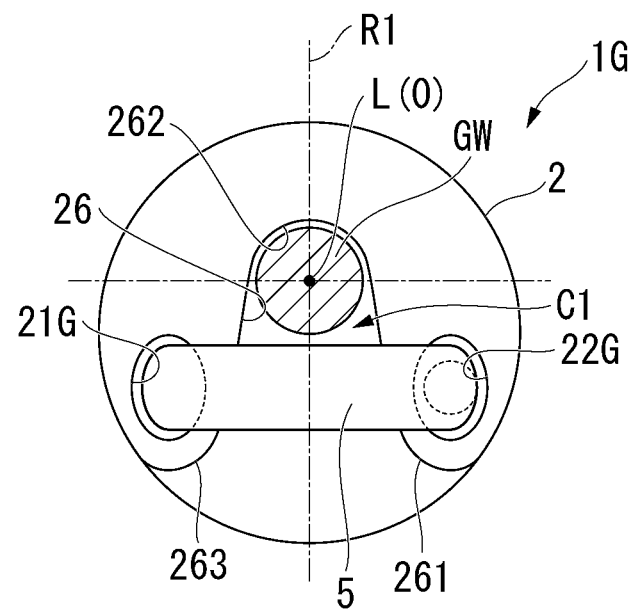
FIG. 21 is a front view of a guide wire holder of a an exemplary embodiment when seen from the distal end.

FIG. 21 is a front view of a guide wire holder 1G of a seventh modified example. The seventh modified example is different from the above-described embodiment in the constitution of the hook 5 and a sheath 2G. In this modified example, a first lumen 21E and a second lumen 22G are formed closer to the outer peripheral opening portion 263 of the groove 26 than the bottom portion 262 of the groove 26. Further, the hook 5 is not curved in the radial direction and extends in the direction of the longitudinal axis L of the sheath 2G (a bending angle θ=180 degrees). Also with such a constitution, the closed region C1 is capable of being formed between the distal end edge 261 of the groove 26 and the hook 5G. Therefore, similarly to the above-described embodiment, the guide wire GW is capable of being held in the closed region C1 while being accommodated in the groove 26, and the sheath 2G is capable of being easily advanced and retracted along the guide wire GW. The bending angle of the hook (refer to FIG. 5) is preferably a right angle or an obtuse angle (90 degrees or more and less than 180 degrees), and as the bending angle θ in this range becomes smaller, a large area of the closed region C1 is capable of being secured in a front view of the distal end of the sheath 2.

Eighth Modified Example

Figure 22:
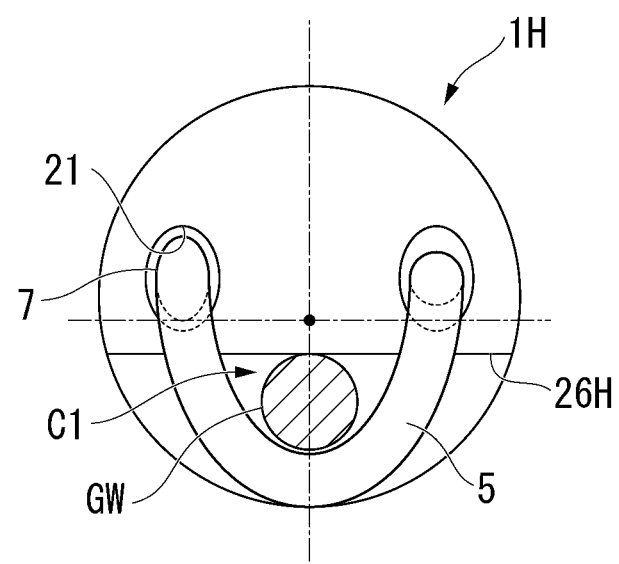
FIG. 22 is a front view of a guide wire holder of an exemplary embodiment when seen from the distal end.

FIG. 22 is a front view of a guide wire holder 1H of an eighth modified example. In the above-described embodiment, although the example in which the groove 26 is provided in the sheath 2 has been shown, the groove 26 is not an essential component, and a ridge line of a side surface of the sheath 2 and the hook 5 may form a closed region in a front view. For example, a part of an outer circumference of the distal end surface of the sheath 2 may have a ridge line which is cut out, and a cutout portion may be a side surface which extends from the distal end to the proximal end. In this modified example, an example in which a distal end portion of a sheath 2H has a flat surface instead of the groove 26 is shown. Specifically, a D-cut portion 26H (a side surface) in which the ridge line of the distal end surface 27 of the sheath 2H has a D shape is formed. A closed region C1 is formed by the D-cut portion 26H and the hook 5. The groove 26 similar to that of the above-described embodiment may be formed on the proximal end side of the D-cut portion 26H.

Ninth Modified Example

Figure 23:
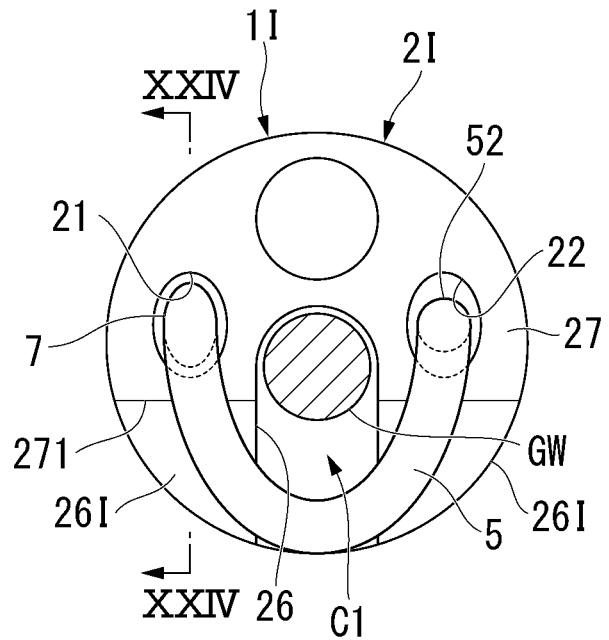
FIG. 23 is a front view of a guide wire holder of an exemplary embodiment when seen from the distal end.
Figure 24:
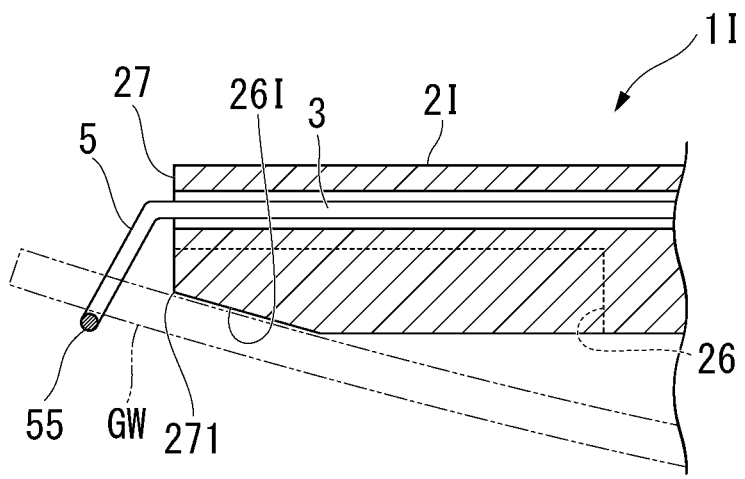
FIG. 24 is a cross-sectional view along line XXIV-XXIV in FIG. 23.

FIG. 23 is a front view of a guide wire holder 1I of a ninth modified example. FIG. 24 is a side view of FIG. 23. In this modified example, in a front view, inclined surfaces (back-cut surfaces) 26I may be provided on both sides of the groove 26 at a distal end portion of a sheath 2I. The inclined surface 26I is inclined from the distal end of the sheath 2I toward the proximal end side. In this case, when the hook 5 is pulled while the guide wire GW is hooked by the hook 5, the guide wire GW easily enters the groove 26.

Tenth Modified Example

Figure 25:
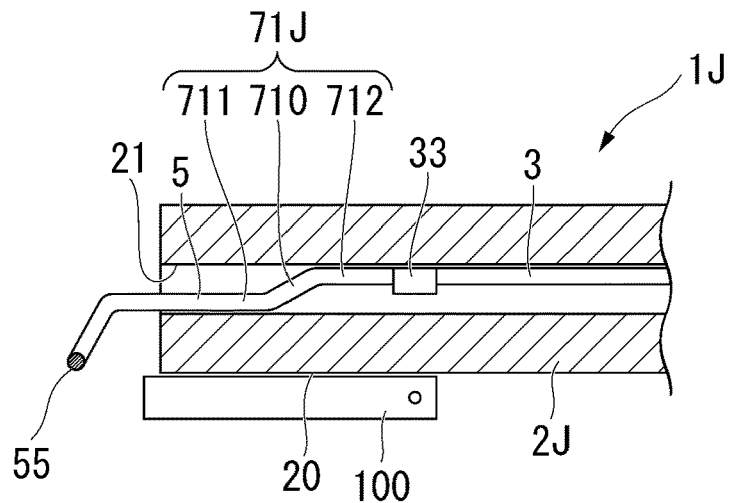
FIG. 25 is a cross-sectional view of a guide wire holder of an exemplary embodiment in a direction of a longitudinal axis.
Figure 26:
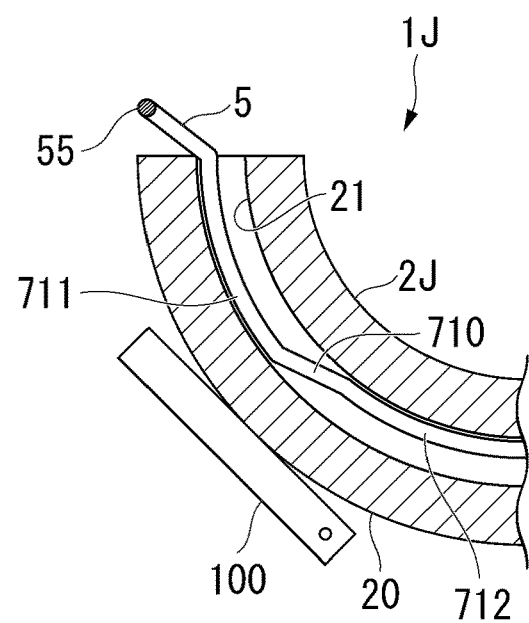
FIG. 26 is a cross-sectional view of the guide wire holder according to an exemplary embodiment in the direction of the longitudinal axis.

FIGS. 25 and 26 are side views of a guide wire holder 1J according to a tenth modified example. The modified example is an example in which a constitution of the restricted portion is different from that of the above-described embodiment. The hook 5 extends to the distal end of the operation wire 3, and the hook 5 and the operation wire 3 are joined by a joint 33. A restricted portion 71J forms a bent portion 710 by bending an intermediate portion of a proximal end region of the hook 5. The restricted portion 71J has a first portion 711 which extends further to the distal end side than the restricted portion 71J and a second portion 712 which extends toward the proximal side. That is, a bent portion between the joint 33 and the hook 5 constitutes the restricted portion 71. In this modified example, the restricted portion 71J is capable of being easily formed only by bending the hook 5.

The first portion 711 is located further outward with respect to the curve of the pre-curved portion 20 than the second portion 712, and the second portion 712 is located further inward with respect to the curve of the pre-curved portion. Further, the first portion 711 and the second portion 712 minimize a clearance to the inner wall of the first lumen 21. Therefore, as shown in FIG. 26, when a sheath 2J is raised by the forceps-elevator 100 provided in the endoscope insertion portion 201, even if a force from the forceps-elevator 100 is applied to the sheath 2J from the outside of the curve of the pre-curved portion 20, the first portion 711 which passes through the inside of the first lumen 21 is unlikely to be displaced inside the curve of the pre-curved portion 20. As a result, a relative position between the second end portion 52 of the hook 5 and the sheath 2J is capable of being prevented from being shifted. Therefore, even when the pre-curved portion 20 is curved by the forceps-elevator 100, a positional relationship between the second lumen 22 and the second end portion 52 is capable of being maintained.

Figure 27:
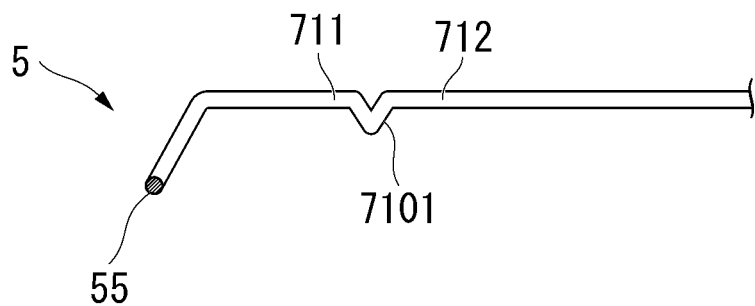
FIG. 27 is a side view showing a modified example of a restricted portion according to an exemplary embodiment.

A shape of the bent portion 710 of the restricted portion 71J is not limited to the shapes shown in FIGS. 25 and 26. For example, the modified example shown in FIG. 27 or 28 may be used. The modified example shown in FIG. 27 is an example in which, when the hook 5 is seen in a direction orthogonal to the longitudinal axis direction of the hook 5, a bent portion 7101 is bent into a V shape, and the first portion 711 and the second portion 712 are located substantially coaxially. The bent portion 7101 is disposed on the groove 26 side or the side surface side in the first lumen. In the case of this modified example, the first portion 711 and the second portion 712, and a vertex portion of the bent portion 7101 are in contact with the first lumen 21 to restrict the rotation of the hook 5 with respect to the sheath 2J.

Figure 28:
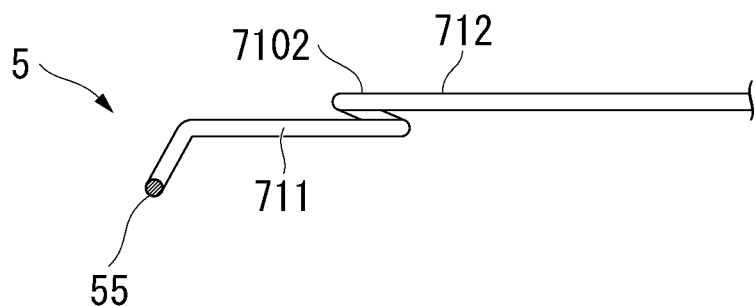
FIG. 28 is a side view showing a modified example of the restricted portion according to an exemplary embodiment.

In the modified example shown in FIG. 28, when the hook 5 is seen in the direction orthogonal to the longitudinal axis direction of the hook 5, a bent portion 7102 is bent into a Z shape, and the first portion 711 and the second portion 712 have their axes offset in the radial direction. In this modified example, when the sheath 2J is raised by the forceps-elevator 100 as in the restricted portion 71J shown in FIG. 25, even if a force from the forceps-elevator 100 is applied to the sheath 2J from the outside of the curve of the pre-curved portion 20, the first portion 711 which passes through the inside of the first lumen 21 is unlikely to be displaced inside the curve of the pre-curved portion 20.

Eleventh Modified Example

Figure 29:
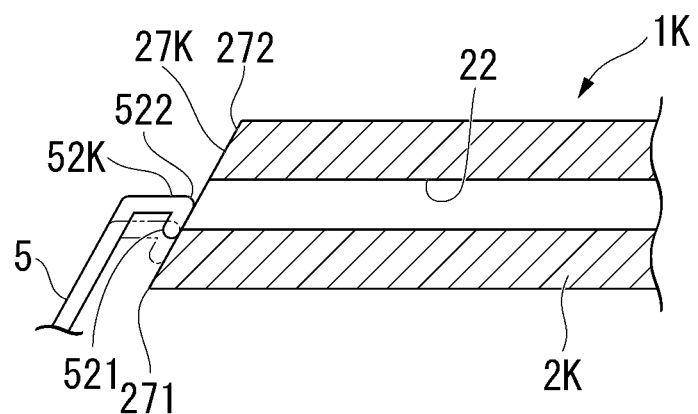
FIG. 29 is a cross-sectional view of a guide wire holder of an exemplary embodiment in the direction of the longitudinal axis.
Figure 30:
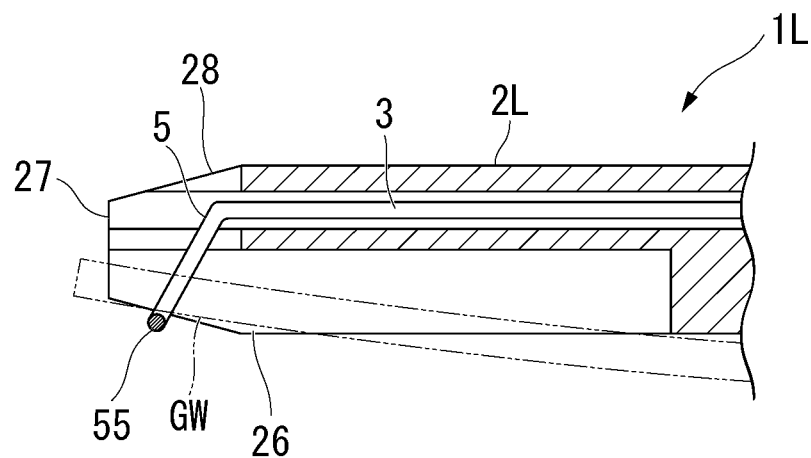
FIG. 30 is a cross-sectional view of a guide wire holder of an exemplary embodiment in the direction of the longitudinal axis.
Figure 31:
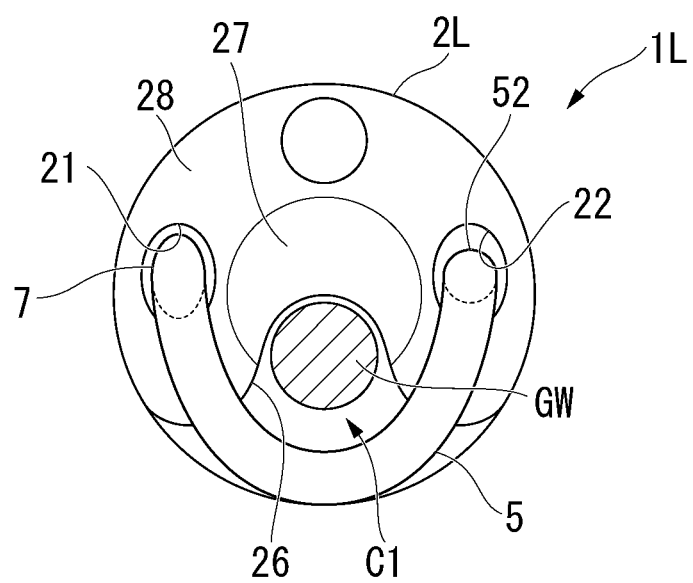
FIG. 31 is a front view of the guide wire holder of an exemplary embodiment when seen from the distal end.
Figure 32:
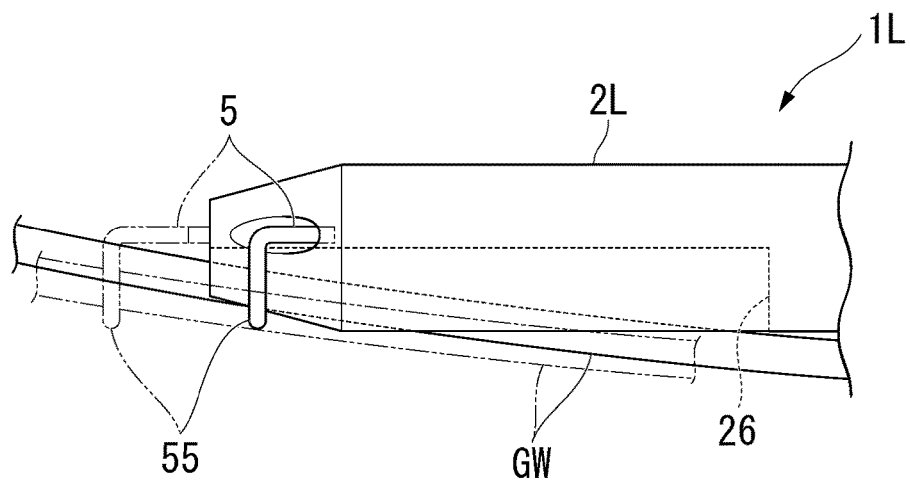
FIG. 32 is a side view of the guide wire holder of an exemplary embodiment.
Figure 33:
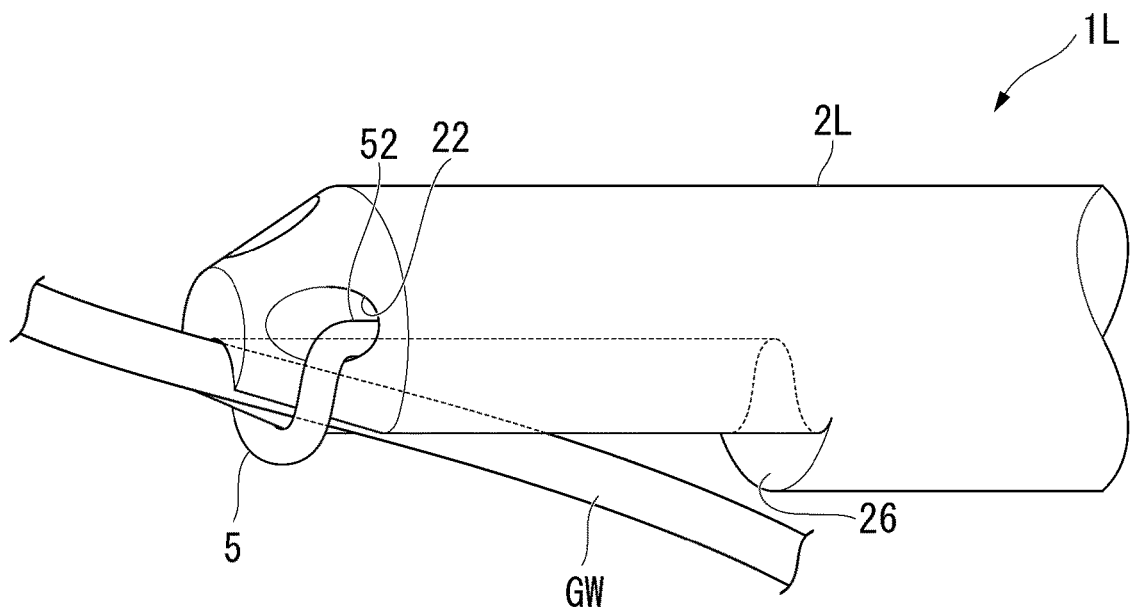
FIG. 33 is a perspective view of the guide wire holder of an exemplary embodiment.

FIG. 29 is a view schematically showing a cross section of a guide wire holder 1K of an eleventh modified example in the longitudinal axis direction. In this modified example, as in the sheath 2F of the sixth modified example, a distal end surface 27K of a sheath 2K is formed to be inclined with respect to the central axis O. A portion 271 of the distal end surface 27K of the sheath 2K on the groove 26 side is inclined to be located on the distal end side. Further, a shape of a second end portion 52K of the hook 5 is different from that in the above-described embodiment. Specifically, a bent portion 522 is formed at a proximal end of the second end portion 52K in direction of the longitudinal axis. The bent portion 522 is folded back in a direction which intersects the longitudinal axis of the second lumen 22, and an end portion 521 extends at the same angle as the inclination angle of the distal end surface 27K. The end portion 521 of the second end portion 52K extends in a direction which intersects the longitudinal axis of the second lumen 22. In this case, when the hook 5 moves toward the proximal side, the end portion 521 comes into contact with the inclination of the distal end surface 27K of the sheath 2 and slides, and thus the second end portion 52K of the hook 5 is easily accommodated in the second lumen 22.

Twelfth Modified Example

FIGS. 30 to 33 show a guide wire holder 1L of a twelfth modified example. The retracted position in which the hook 5 is most retracted with respect to a sheath 2L may be located closer to the proximal end side than the distal end of the sheath 2L. As shown in the cross-sectional view in the direction of the longitudinal axis of FIG. 30, the sheath 2L may include a tapered portion 28 of which a diameter of a distal end portion is reduced. When such a tapered portion 28 is provided, the sheath 2L is capable of being smoothly inserted into the duodenum D. Further, when the hook 5 is at the retracted position at which it is most retracted with respect to the sheath 2L, the hook 5 is located closer to the proximal end side than the distal end of the sheath 2L. Therefore, since the hook 5 is located closer to the proximal end side than the distal end of the sheath 2L, the sheath 2L is capable of being easily inserted into the duodenal papilla Dp. Further, a length of the separation distance LS between the second end portion 52 and the distal end of the sheath 2 at the advanced position is capable of being adjusted according to the advance and retract of the hook 5. When the separation distance LS between the second end portion 52 and the distal end of the sheath 2L is larger than the diameter of the guide wire GW, the guide wire GW is capable of being inserted into a space between the second end portion 52 and the distal end of the sheath 2L. When the guide wire GW is held between the hook 5 and the side surface of the groove 26, the separation distance LS is set to be smaller than the diameter of the guide wire GW, and thus the guide wire GW does not come off from the closed region C1. As a result, the guide wire holder 1L is capable of curbing the distal end portion of the sheath 2L to a small dimension while holding the guide wire GW and thus the sheath 2L is capable of easily inserting into the duodenal papilla Dp.

Thirteenth Modified Example

Figure 34:
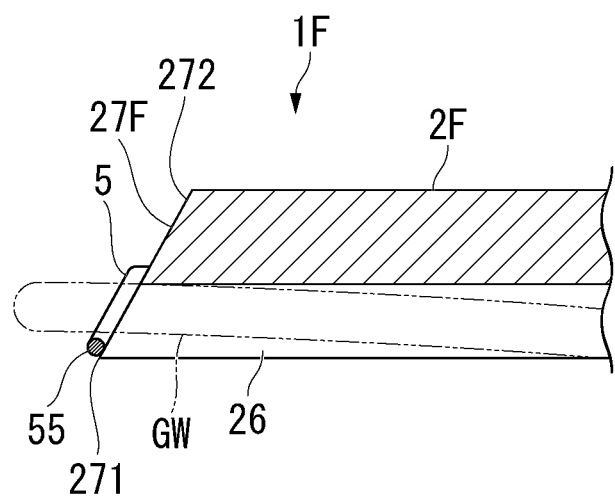
FIG. 34 is a cross-sectional view of a guide wire holder of an exemplary embodiment in the direction of the longitudinal axis.

As for the shaft of the distal end of the sheath in each of the embodiment and the modified examples, the distal end surface 27F of the sheath 2F may be inclined to have a tapered shape as in a thirteenth modified example shown in FIG. 34. Since the distal end surface 27F of the sheath 2F is inclined to have the tapered shape in this way, the sheath 2F is easily inserted into the duodenal papilla Dp.

Although one embodiment of the present invention has been described above, the technical scope of the present invention is not limited to the above-described embodiment, and it is possible to add various changes to each of the components, to delete each of the components, or to combine the components of each of the embodiments without departing from the spirit of the present invention.

What is claimed is:
1. A guide wire holder, comprising:
   a sheath including a lumen, a central axis of the sheath extending along a longitudinal axis;
   an operation wire configured to be inserted into the lumen and configured to advance and retract in the lumen along the longitudinal axis; and
   a hook that is continuous with a distal end of the operation wire and protrudes from a distal end of the sheath,
   wherein:
      the sheath has a side surface that extends from the distal end of the sheath to a proximal side in a direction of the longitudinal axis,
      the side surface includes a groove that is formed in a concave shape at a part of an outer periphery of the sheath,
      the groove is recessed in a radial direction of the sheath so as to have a groove depth along the radial direction of the sheath and an opening formed between opposing surfaces of the sheath in a width direction orthogonal to the groove depth and orthogonal to the longitudinal axis, and
      an opening width of the groove between the opposing surfaces of the sheath in the width direction widens from a bottom portion of the groove outwardly along the radial direction at least at a distal end portion of the sheath.
2. The guide wire holder according to claim 1, wherein:
   the hook is bent at a right angle with respect to the central axis of the lumen from a side view, and
   the hook is configured to be able to capture the guide wire in a state in which the guide wire is arranged from the side surface toward the proximal end side of the sheath along the direction of the longitudinal axis.
3. The guide wire holder according to claim 1, wherein:
   the hook includes a first end portion that is connected to the distal end of the operation wire, and a second end portion which extends along the longitudinal axis toward a proximal end side of the sheath;
   the hook is configured to be positioned in an advanced position and a retracted position;
   the second end portion is spaced from the distal end of the sheath in the advanced position;
   the second end portion intersects the distal end of the sheath in the retracted position;
   the sheath includes a hook-accommodating lumen, the hook-accommodating lumen defining an inner diameter larger than an outer diameter of the second end portion,
   the second end portion can fit in the hook-accommodating lumen by retracting the operation wire, and
   when the second end portion is accommodated in the hook-accommodating lumen, the hook protrudes from the sheath and is configured to hold the guide wire between the side surface and a portion protruding from the sheath.
4. The guide wire holder according to claim 1, wherein the side surface at a part of an outer periphery of a distal end surface of the sheath includes a cut out and the cut out extends from the distal end toward a proximal end of the sheath.
5. The guide wire holder according to claim 1, wherein the hook and the side surface are disposed so that the guide wire is configured to advance and retract between the hook and the side surface.
6. The guide wire holder according to claim 1, wherein the side surface which forms the groove is a curved surface.
7. The guide wire holder according to claim 1, wherein the hook and the groove are disposed so that the guide wire is configured to advance and retract between the hook and the groove.

8. The guide wire holder according to claim 1, wherein:
the sheath has inclined surfaces formed on both sides of the groove, and
the inclined surfaces incline from the distal end of the sheath toward a proximal side of the sheath.

9. The guide wire holder according to claim 1, wherein, when the guide wire is held between the hook and the groove, at least a part of the hook does not contact a distal end of the groove.

10. The guide wire holder according to claim 1, wherein the side surface is a flat surface.

11. The guide wire holder according to claim 1, comprising a rotation-preventing portion including a restricting portion provided in at least a part of the lumen in the direction of the longitudinal axis and in which an opening shape of the lumen in a cross section orthogonal to the longitudinal axis is an elliptical, and a restricted portion which is provided in at least a part of the operation wire in an axis direction, has an elliptical cross-sectional shape orthogonal to the longitudinal axis and configured to advance and retract in the restricting portion, the rotation-preventing portion being configured so that a direction around the longitudinal axis of the operation wire is restricted.

12. The guide wire holder according to claim 11, wherein:
the restricting portion is provided at a distal end portion of the lumen, and
a proximal end of the restricted portion is disposed in the lumen.

13. The guide wire holder according to claim 1, wherein:
the hook extends to the distal end of the operation wire,
the sheath includes a restricting portion provided in at least a part of the lumen in the direction of the longitudinal axis and in which an opening shape of the lumen in a cross section orthogonal to the longitudinal axis is an elliptical,
the hook has a restricted portion formed by bending a rod-shaped member, and
rotation of the operation wire around the axis is restricted by locking the restricting portion to the restricted portion.

14. The guide wire holder according to claim 13, wherein:
a distal end portion of the sheath has a pre-curved portion in which the longitudinal axis is curved,
a portion of the hook that fits in the lumen has a first portion which extends further toward a distal side than the restricted portion and a second portion which extends toward a proximal side further than the restricted portion,
the first portion is located further outward with respect to a curve of the pre-curved portion from the second portion, and
the second portion is located further inward with respect to the curve of the pre-curved portion from the first portion.

15. The guide wire holder according to claim 3, wherein:
the distal end of the sheath has an inclined surface which is inclined from the proximal side toward the distal side in a tapered shape, and
the second end portion of the hook is folded back in a direction intersecting the longitudinal axis of the hook-accommodating lumen.

16. The guide wire holder according to claim 1, wherein the hook is bent at an obtuse angle with respect to the central axis of the lumen from a side view.

17. The guide wire holder according to claim 1, wherein:
the hook intersects a ridge line of the side surface and forms a closed region in a front view of the distal end of the sheath and the hook when viewed from a distal side to proximal side along the longitudinal axis, and
the guide wire holder is configured to hold guide wire located outside the sheath in the closed region in a state in which the hook is disposed at a retracted position.

18. The guide wire holder according to claim 17, wherein:
when viewed from the front view, a boundary of the groove is the ridge line,
when viewed from the front view, the closed region is defined by a boundary of the hook and the ridge line, and
when viewed from the front view, the hook is curved toward the groove along the radial direction of the sheath.

19. The guide wire holder according to claim 1, wherein:
the hook is curved to form a U-shape in a front view of the distal end of the hook when viewed from a distal side to proximal side along the longitudinal axis.

20. The guide wire holder according to claim 1, wherein:
the hook is curved toward the groove along the radial direction of the sheath in a front view of the distal end of the hook when viewed from a distal side to proximal side along the longitudinal axis.

* * * * *